(12) United States Patent
Wu

(10) Patent No.: US 9,421,530 B2
(45) Date of Patent: *Aug. 23, 2016

(54) METHODS OF REGENERATING AROMATIZATION CATALYSTS

(71) Applicant: Chevron Phillips Chemical Company LP, The Woodlands, TX (US)

(72) Inventor: An-Hsiang Wu, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/927,939

(22) Filed: Oct. 30, 2015

(65) Prior Publication Data

US 2016/0045904 A1 Feb. 18, 2016

Related U.S. Application Data

(63) Continuation of application No. 14/542,856, filed on Nov. 17, 2014, now Pat. No. 9,174,895, which is a continuation of application No. 13/758,144, filed on Feb. 4, 2013, now Pat. No. 8,912,108, which is a continuation-in-part of application No. 13/412,399, filed on Mar. 5, 2012, now Pat. No. 8,716,161.

(51) Int. Cl.
| | |
|---|---|
| *B01J 38/46* | (2006.01) |
| *B01J 29/90* | (2006.01) |
| *C10G 35/095* | (2006.01) |
| *B01J 38/12* | (2006.01) |
| *B01J 29/62* | (2006.01) |
| *C10G 35/06* | (2006.01) |
| *C10G 45/70* | (2006.01) |
| *C07C 5/367* | (2006.01) |
| *C07C 5/41* | (2006.01) |
| *B01J 29/74* | (2006.01) |
| *B01J 38/44* | (2006.01) |
| *B01J 38/42* | (2006.01) |

(52) U.S. Cl.
CPC *B01J 29/90* (2013.01); *B01J 29/62* (2013.01); *B01J 29/74* (2013.01); *B01J 38/12* (2013.01); *B01J 38/44* (2013.01); *B01J 38/46* (2013.01); *C07C 5/367* (2013.01); *C07C 5/412* (2013.01); *C07C 5/417* (2013.01); *C10G 35/06* (2013.01); *C10G 35/095* (2013.01); *C10G 45/70* (2013.01); *B01J 38/42* (2013.01); *C07C 2529/068* (2013.01); *C07C 2529/74* (2013.01); *C10G 2300/708* (2013.01)

(58) Field of Classification Search
CPC .......................................................... B01J 38/46
USPC .......................................................... 502/36
See application file for complete search history.

(56) References Cited

U.S. PATENT DOCUMENTS

| | | |
|---|---|---|
| 2,906,702 A | 9/1959 | Brennan et al. |
| 3,898,173 A | 8/1975 | Hayes |
| 3,941,716 A | 3/1976 | Paynter |
| 3,969,267 A | 7/1976 | McVicker |
| 4,094,814 A | 6/1978 | Lemberger et al. |
| 4,104,320 A | 8/1978 | Bernard et al. |
| 4,435,283 A | 3/1984 | Buss et al. |
| 4,444,895 A | 4/1984 | Fung et al. |
| 4,444,896 A | 4/1984 | Fung et al. |
| 4,444,897 A | 4/1984 | Fung et al. |
| 4,447,551 A | 5/1984 | Fung et al. |
| 4,456,527 A | 6/1984 | Buss et al. |
| 4,467,045 A | 8/1984 | Fung |
| 4,472,514 A | 9/1984 | Fung |
| 4,472,515 A | 9/1984 | Fung |
| 4,473,656 A | 9/1984 | Fung et al. |
| 4,480,046 A | 10/1984 | Fung et al. |
| 4,491,635 A | 1/1985 | Fung et al. |
| 4,491,636 A | 1/1985 | Fung et al. |
| 4,492,767 A | 1/1985 | Fung |
| 4,493,901 A | 1/1985 | Bernard et al. |
| 4,539,304 A | 9/1985 | Field |
| 4,547,472 A | 10/1985 | Van Nordstrand |
| 4,552,856 A | 11/1985 | Tauster et al. |
| 4,595,668 A | 6/1986 | Poeppelmeier et al. |
| 4,595,669 A | 6/1986 | Fung et al. |
| 4,595,670 A | 6/1986 | Tauster et al. |
| 4,634,517 A | 1/1987 | Tauster et al. |
| 4,634,518 A | 1/1987 | Buss et al. |
| 4,645,751 A | 2/1987 | McCullen et al. |
| 4,648,960 A | 3/1987 | Poeppelmeier et al. |

(Continued)

FOREIGN PATENT DOCUMENTS

| | | |
|---|---|---|
| EP | 0 145 289 | 6/1985 |
| EP | 0 278 851 | 8/1988 |

(Continued)

OTHER PUBLICATIONS

Ko, et al., "Synthesis and Characterization of Zeolite L," published in the Bull. Korean Chem. Soc. 1999, vol. 20, No. 2. 6 pages.
Fung S.C., "Deactivation and Regeneration/Redispersion Chemistry of Pt/KL-Zeolite," published in Studies in Surface Science and Catalysis, 2001, vol. 139, pp. 399-406, Elsevier Publisher.
Fukunaga, et al., "Halogen-promoted Pt/KL Zeolite Catalyst for the Production of Aromatic Hydrocarbons from Light Naphtha," published in Catal. Surv. Asia, (2010), vol. 14, pp. 96-102, Springer Science+Business Media, LLC.
Grau et al., "Heptane Dehydrocyclization Over Pt/KL Catalysts Doped with Barium or Lanthanum," published in *Catalysis Letters* vol. 83, Nov. 2002, pp. 247-255.

(Continued)

*Primary Examiner* — Edward Johnson
(74) *Attorney, Agent, or Firm* — Merchant & Gould P.C.

(57) ABSTRACT

Methods for treating or rejuvenating a spent catalyst are disclosed. Such methods can employ a step of halogenating the spent catalyst, followed by decoking the halogenated spent catalyst. The halogenation step can utilize fluorine and chlorine together, or fluorine and chlorine can be applied sequentially.

20 Claims, No Drawings

(56) References Cited

U.S. PATENT DOCUMENTS

| | | |
|---|---|---|
| 4,657,874 A | 4/1987 | Borghard et al. |
| 4,678,764 A | 7/1987 | Le et al. |
| 4,681,865 A | 7/1987 | Katsuno et al. |
| 4,721,607 A | 1/1988 | Haddad et al. |
| 4,721,694 A | 1/1988 | Buss et al. |
| 4,789,655 A | 12/1988 | Travers et al. |
| 4,810,683 A | 3/1989 | Cohn et al. |
| 4,822,762 A | 4/1989 | Ellig et al. |
| 4,824,816 A | 4/1989 | Trowbridge et al. |
| 4,835,129 A | 5/1989 | Travers et al. |
| 4,839,320 A | 6/1989 | Trowbridge et al. |
| 4,851,380 A | 7/1989 | Van Leirsburg et al. |
| 4,855,269 A | 8/1989 | Mohr |
| 4,872,970 A | 10/1989 | Boyle |
| 4,914,068 A | 4/1990 | Cross et al. |
| 4,925,819 A | 5/1990 | Fung et al. |
| 4,937,215 A | 6/1990 | Murakawa et al. |
| 5,028,312 A | 7/1991 | Miller et al. |
| 5,034,117 A | 7/1991 | De Bonneville et al. |
| 5,106,798 A | 4/1992 | Fung |
| 5,106,803 A | 4/1992 | Mohr et al. |
| 5,155,074 A | 10/1992 | Mohr |
| 5,185,306 A | 2/1993 | Cohn et al. |
| 5,196,631 A | 3/1993 | Murakawa et al. |
| RE34,250 E | 5/1993 | Van Leirsburg et al. |
| 5,220,108 A | 6/1993 | Hashimoto et al. |
| 5,256,612 A | 10/1993 | Fung |
| 5,260,238 A | 11/1993 | Murakawa et al. |
| 5,270,272 A | 12/1993 | Galperin et al. |
| 5,348,924 A | 9/1994 | Potter et al. |
| 5,378,669 A | 1/1995 | Fung |
| 5,389,235 A | 2/1995 | Russ et al. |
| 5,401,365 A | 3/1995 | Chen et al. |
| 5,401,386 A | 3/1995 | Morrison et al. |
| 5,491,119 A | 2/1996 | Verduijn |
| 5,552,035 A | 9/1996 | Potter et al. |
| 5,557,029 A | 9/1996 | Lin et al. |
| 5,573,988 A | 11/1996 | Didillon |
| 5,672,801 A | 9/1997 | Didillon |
| 5,683,573 A | 11/1997 | Haizmann et al. |
| 5,698,486 A | 12/1997 | Fung et al. |
| 5,712,214 A | 1/1998 | Huang et al. |
| 5,726,112 A | 3/1998 | Fung et al. |
| 5,755,956 A | 5/1998 | Galperin et al. |
| 5,756,414 A | 5/1998 | Huang et al. |
| 5,763,348 A | 6/1998 | Fung et al. |
| 5,776,849 A | 7/1998 | Fung et al. |
| 5,792,338 A | 8/1998 | Gosling et al. |
| 5,854,162 A | 12/1998 | Dufresne et al. |
| 5,866,495 A | 2/1999 | Fung et al. |
| 5,880,049 A | 3/1999 | Lacroix et al. |
| 5,880,050 A | 3/1999 | Boitiaux et al. |
| 5,883,031 A | 3/1999 | Innes et al. |
| 5,898,011 A | 4/1999 | Wu et al. |
| 5,935,415 A | 8/1999 | Haizmann et al. |
| 5,980,731 A | 11/1999 | Kao et al. |
| 6,034,019 A | 3/2000 | Fung et al. |
| 6,048,814 A | 4/2000 | Capelle et al. |
| 6,103,652 A | 8/2000 | Brunet et al. |
| 6,110,857 A | 8/2000 | Fung et al. |
| 6,133,183 A | 10/2000 | Capelle et al. |
| 6,143,166 A | 11/2000 | Nacamuli |
| 6,147,022 A | 11/2000 | Brunet et al. |
| 6,190,539 B1 | 2/2001 | Holtermann et al. |
| 6,191,332 B1 | 2/2001 | Duee et al. |
| 6,207,042 B1 | 3/2001 | Holtermann et al. |
| 6,277,335 B1 | 8/2001 | Capelle et al. |
| 6,291,381 B1 | 9/2001 | Lin et al. |
| 6,294,492 B1 | 9/2001 | Lin |
| 6,348,144 B1 | 2/2002 | Gevelinger |
| 6,358,400 B1 | 3/2002 | Bogdan et al. |
| 6,380,119 B1 | 4/2002 | Grosch et al. |
| 6,406,614 B1 | 6/2002 | Tiedtke et al. |
| 6,410,472 B2 | 6/2002 | Macahan et al. |
| 6,426,052 B1 | 7/2002 | Capelle et al. |
| 6,461,992 B1 | 10/2002 | Sechrist et al. |
| 6,472,340 B2 | 10/2002 | Lin |
| 6,518,470 B1 | 2/2003 | Fukunaga et al. |
| 6,593,264 B2 | 7/2003 | Lin et al. |
| 6,600,082 B2 | 7/2003 | Le Peltier et al. |
| 6,605,566 B2 | 8/2003 | Le Peltier et al. |
| 6,710,002 B2 | 3/2004 | Grosch et al. |
| 6,740,615 B2 | 5/2004 | Zhou |
| 6,784,132 B1 | 8/2004 | Sechrist |
| 6,790,802 B1 | 9/2004 | Sechrist |
| 6,812,180 B2 | 11/2004 | Fukunaga |
| 6,833,338 B2 | 12/2004 | McDaniel et al. |
| 6,881,391 B1 | 4/2005 | Sechrist |
| 6,908,873 B2 | 6/2005 | Zhou et al. |
| 7,037,871 B1 | 5/2006 | Galperin et al. |
| 7,074,975 B2 | 7/2006 | Braun et al. |
| 7,153,801 B2 | 12/2006 | Wu |
| 7,223,710 B1 | 5/2007 | Sechrist |
| 7,312,173 B1 | 12/2007 | Yuan et al. |
| 7,319,175 B2 | 1/2008 | Braun et al. |
| 7,582,272 B2 | 9/2009 | Glova et al. |
| 7,638,101 B2 | 12/2009 | Yuan et al. |
| 7,745,675 B2 | 6/2010 | Ellis et al. |
| 7,868,217 B2 | 1/2011 | Brown et al. |
| 7,932,425 B2 | 4/2011 | Blessing et al. |
| 7,985,381 B2 | 7/2011 | Sun et al. |
| 8,216,522 B2 | 7/2012 | Sun et al. |
| 8,664,144 B2 | 3/2014 | Wu |
| 8,716,161 B2 | 5/2014 | Wu |
| 8,912,108 B2 | 12/2014 | Wu |
| 9,174,895 B2 * | 11/2015 | Wu ........................ B01J 29/90 |
| 2004/0259719 A1 | 12/2004 | Wu |
| 2005/0027648 A1 | 2/2005 | Knowles et al. |
| 2010/0160147 A1 | 6/2010 | Wu |
| 2010/0160150 A1 | 6/2010 | Wu |
| 2010/0160702 A1 | 6/2010 | Wu |
| 2010/0222202 A1 | 9/2010 | Nabozny et al. |
| 2012/0093699 A1 | 4/2012 | Nabozny et al. |
| 2013/0231511 A1 | 9/2013 | Wu |
| 2014/0088333 A1 | 3/2014 | Khare |
| 2014/0213839 A1 | 7/2014 | Wu |
| 2015/0073190 A1 | 3/2015 | Wu |

FOREIGN PATENT DOCUMENTS

| | | |
|---|---|---|
| EP | 0 316 727 | 5/1989 |
| EP | 0 378 482 | 7/1990 |
| EP | 0 294 448 | 8/1991 |
| EP | 0 294 477 | 9/1992 |
| EP | 0 334 562 | 3/1993 |
| EP | 0 535 619 | 4/1993 |
| EP | 0 548 421 | 6/1993 |
| EP | 0 710 502 | 5/1996 |
| EP | 0 872 276 | 10/1998 |
| EP | 0 872 277 | 10/1998 |
| EP | 0 873 785 | 10/1998 |
| FR | 2 325 289 | 4/1977 |
| GB | 760612 | 11/1956 |
| WO | WO 86/02861 | 5/1986 |
| WO | WO 96/24834 | 8/1996 |
| WO | WO 98/47615 | 10/1998 |
| WO | WO 2010/075133 | 7/2010 |
| WO | WO 2010/075134 | 7/2010 |
| WO | WO 2010/075135 | 7/2010 |

OTHER PUBLICATIONS

International Application PCT/US2013/028533 Search Report dated Jun. 20, 2013, 4 pages.
International Search Report and Written Opinion, in Application No. PCT/US2009/068267, dated Jun. 30, 2010, 18 pages.
International Search Report and Written Opinion, in Application No. PCT/US2009/068266, dated May 25, 2010, 17 pages.
International Search Report and Written Opinion, in Application No. PCT/US2009/068268, dated Aug. 26, 2010, 22 pages.
International Search Report and Written Opinion in Application No. PCT/US2013/061370, dated Dec. 13, 2013, 10 pages.
Official Action in U.S. Appl. No. 12/617,440 dated Aug. 5, 2011, 32 pages.

(56) References Cited

OTHER PUBLICATIONS

Official Action in U.S. Appl. No. 12/617,440 dated Feb. 13, 2012, 15 pages.
Official Action/Advisory Action in U.S. Appl. No. 12/617,440 dated Apr. 18, 2012, 4 pages.
Official Action in U.S. Appl. No. 12/617,440 dated Jun. 13, 2012, 18 pages.
Official Action/Advisory Action in U.S. Appl. No. 12/617,440 dated Sep. 6, 2012, 5 pages.
Official Action in U.S. Appl. No. 12/617,440 dated Mar. 5, 2013, 19 pages.
Official Action in U.S. Appl. No. 12/617,440 dated Jul. 9, 2013, 15 pages.
Official Action in U.S. Appl. No. 13/758,144 dated May 9, 2014 (19 pages) (80usi1).

* cited by examiner

METHODS OF REGENERATING AROMATIZATION CATALYSTS

REFERENCE TO RELATED APPLICATION

This application is a continuation application of U.S. patent application Ser. No. 14/542,856, filed on Nov. 17, 2014, now U.S. Pat. No. 9,174,895, which is a continuation application of U.S. patent application Ser. No. 13/758,144, filed on Feb. 4, 2013, now U.S. Pat. No. 8,912,108, which is a continuation-in-part application of U.S. patent application Ser. No. 13/412,399, filed on Mar. 5, 2012, now U.S. Pat. No. 8,716,161, which are incorporated herein by reference in their entirety.

BACKGROUND OF THE INVENTION

The catalytic conversion of non-aromatic hydrocarbons into aromatic compounds, often referred to as aromatization or reforming, is an important industrial process that can be used to produce benzene, toluene, xylene, and the like. The aromatization or reforming process often is conducted in a reactor system that can contain one or more reactors containing transition metal based catalysts. These catalysts can increase the selectivity to and/or the yield of the desired aromatic compounds. However, under commercial reaction conditions, these catalysts slowly lose their activity, often indicated by a loss of selectivity to desired aromatic compounds and/or a reduction in conversion rates. Such catalysts are often referred to as "spent" catalysts once economic or operational thresholds are passed.

Because of their commercial importance and the expense incurred in producing fresh catalyst to replace spent catalyst, there is an ongoing need for improved methods of restoring catalytic activity to spent aromatization catalysts. Accordingly, it is to this end that the present disclosure is directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Methods for treating or regenerating spent catalysts comprising a transition metal and a catalyst support are disclosed and described herein. One such method of treating or regenerating a spent catalyst can comprise (i) contacting the spent catalyst with a halogen-containing stream comprising chlorine and fluorine to produce a halogenated spent catalyst; and (ii) contacting the halogenated spent catalyst with a decoking gas stream comprising oxygen.

Another method of treating or regenerating a spent catalyst can comprise (1) contacting the spent catalyst with a fluorine-containing stream comprising a fluorine-containing compound to produce a fluorinated spent catalyst; (2) contacting the fluorinated spent catalyst with a chlorine-containing stream comprising a chlorine-containing compound to produce a fluorinated-chlorinated spent catalyst; and (3) contacting the fluorinated-chlorinated spent catalyst with a decoking gas stream comprising oxygen.

Yet another method of treating or regenerating a spent catalyst can comprise (1) contacting the spent catalyst with a chlorine-containing stream comprising a chlorine-containing compound to produce a chlorinated spent catalyst; (2) contacting the chlorinated spent catalyst with a fluorine-containing stream comprising a fluorine-containing compound to produce a chlorinated-fluorinated spent catalyst; and (3) contacting the chlorinated-fluorinated spent catalyst with a decoking gas stream comprising oxygen.

Also disclosed herein are various processes for reforming hydrocarbons. One such reforming process can comprise (a) contacting a hydrocarbon feed with an aromatization catalyst comprising a transition metal and a catalyst support under reforming conditions in a reactor system to produce an aromatic product; (b) performing step (a) for a time period sufficient to form a spent aromatization catalyst; (c) contacting the spent aromatization catalyst with a halogen-containing stream comprising chlorine and fluorine to produce a halogenated spent catalyst; and (d) contacting the halogenated spent catalyst with a decoking gas stream comprising oxygen.

Another process for reforming hydrocarbons can comprise (A) contacting a hydrocarbon feed with an aromatization catalyst comprising a transition metal and a catalyst support under reforming conditions in a reactor system to produce an aromatic product; (B) performing step (A) for a time period sufficient to form a spent aromatization catalyst; (C) contacting the spent aromatization catalyst with a fluorine-containing stream comprising a fluorine-containing compound to produce a fluorinated spent catalyst; (D) contacting the fluorinated spent catalyst with a chlorine-containing stream comprising a chlorine-containing compound to produce a fluorinated-chlorinated spent catalyst; and (E) contacting the fluorinated-chlorinated spent catalyst with a decoking gas stream comprising oxygen.

Yet another process for reforming hydrocarbons can comprise (A) contacting a hydrocarbon feed with an aromatization catalyst comprising a transition metal and a catalyst support under reforming conditions in a reactor system to produce an aromatic product; (B) performing step (A) for a time period sufficient to form a spent aromatization catalyst; (C) contacting the spent aromatization catalyst with a chlorine-containing stream comprising a chlorine-containing compound to produce a chlorinated spent catalyst; (D) contacting the chlorinated spent catalyst with a fluorine-containing stream comprising a fluorine-containing compound to produce a chlorinated-fluorinated spent catalyst; and (E) contacting the chlorinated-fluorinated spent catalyst with a decoking gas stream comprising oxygen.

Both the foregoing summary and the following detailed description provide examples and are explanatory only. Accordingly, the foregoing summary and the following detailed description should not be considered to be restrictive. Further, features or variations may be provided in addition to those set forth herein. For example, certain embodiments may be directed to various feature combinations and sub-combinations described in the detailed description.

DEFINITIONS

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Regarding claim transitional terms or phrases, the transitional term "comprising," which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claim. A "consisting essentially of" claim occupies a middle ground between closed claims that are written in a "consisting of" format and fully open claims that are drafted in a "comprising" format. For example, absent an indication to the contrary, describing a compound or composition as "consisting essentially of" is not to be construed as "comprising," but is intended to describe the recited component that includes materials which do not significantly alter the composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to the feature class to which it is utilized, and it is possible to have different transitional terms or phrases utilized with different features within a claim. For example, a method can comprise several recited steps (and other non-recited steps), but utilize a catalyst system consisting of specific components; alternatively, consisting essentially of specific components; or alternatively, comprising the specific components and other non-recited components.

In this disclosure, while compositions and methods are often described in terms of "comprising" various components or steps, the compositions and methods can also "consist essentially of" or "consist of" the various components or steps, unless stated otherwise.

The terms "a," "an," and "the" are intended to include plural alternatives, e.g., at least one. For instance, the disclosure of "a transition metal," "a halogen-containing compound," etc., is meant to encompass one, or mixtures or combinations of more than one, transition metal, halogen-containing compound, etc., unless otherwise specified.

A "spent" catalyst is used herein generally to describe a catalyst that has unacceptable performance in one or more of catalyst activity, hydrocarbon feed conversion, yield to a desired product(s), selectivity to a desired product(s), or an operating parameter, such as output/production rate or reforming temperature, although the determination that a catalyst is "spent" is not limited only to these features. In some embodiments, the fresh catalyst can have an activity X, the spent catalyst can have an activity Z, and the treated or rejuvenated catalyst can have an activity Y, such that Z<Y<X. In certain embodiments disclosed herein, the rejuvenated catalyst often can have an activity that is from about 50% to about 80% of the activity of the fresh catalyst (e.g., Y=about 0.5× to about 0.8×). Such catalyst activity comparisons are meant to use the same production run (batch) of catalyst, tested on the same equipment, and under the same test method and conditions.

For any particular compound or group disclosed herein, any name or structure (general or specific) presented is intended to encompass all conformational isomers, regioisomers, stereoisomers, and mixtures thereof that can arise from a particular set of substituents, unless otherwise specified. The name or structure (general or specific) also encompasses all enantiomers, diastereomers, and other optical isomers (if there are any) whether in enantiomeric or racemic forms, as well as mixtures of stereoisomers, as would be recognized by a skilled artisan, unless otherwise specified. For example, a general reference to pentane, for example, includes n-pentane, 2-methyl-butane, and 2,2-dimethylpropane; and a general reference to a butyl group includes a n-butyl group, a sec-butyl group, an iso-butyl group, and a t-butyl group.

In one embodiment, a chemical "group" can be defined or described according to how that group is formally derived from a reference or "parent" compound, for example, by the number of hydrogen atoms removed from the parent compound to generate the group, even if that group is not literally synthesized in such a manner. These groups can be utilized as substituents or coordinated or bonded to metal atoms. By way of example, an "alkyl group" formally can be derived by removing one hydrogen atom from an alkane. The disclosure that a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedures, unless specified otherwise or the context requires otherwise.

Various numerical ranges are disclosed herein. When Applicants disclose or claim a range of any type, Applicants' intent is to disclose or claim individually each possible number that such a range could reasonably encompass, including end points of the range as well as any sub-ranges and combinations of sub-ranges encompassed therein, unless otherwise specified. As a representative example, Applicants disclose that the methods provided herein can employ a halogen-containing stream containing Cl and F at a molar ratio of Cl:F in a range from about 0.1:1 to about 20:1 in certain embodiments. By a disclosure that the molar ratio of Cl:F in the halogen-containing stream can be in a range from about 0.1:1 to about 20:1, Applicants intend to recite that the molar ratio can be about 0.1:1, about 0.2:1, about 0.3:1, about 0.4:1, about 0.5:1, about 0.6:1, about 0.7:1, about 0.8:1, about 0.9:1, about 1:1, about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, or about 20:1. Additionally, the molar ratio of Cl:F can be within any range from about 0.1:1 to about 20:1 (for example, the molar ratio can be in a range from about 0.2:1 to about 10:1), and this also includes any combination of ranges between about 0.1:1 and about 20:1. Likewise, all other ranges disclosed herein should be interpreted in a manner similar to this example.

Applicants reserve the right to proviso out or exclude any individual members of any such group, including any sub-ranges or combinations of sub-ranges within the group, that can be claimed according to a range or in any similar manner, if for any reason Applicants choose to claim less than the full measure of the disclosure, for example, to account for a reference that Applicants may be unaware of at the time of the filing of the application. Further, Applicants reserve the right to proviso out or exclude any individual substituents, analogs, compounds, ligands, structures, or groups thereof, or any members of a claimed group, if for any reason Applicants choose to claim less than the full measure of the disclosure, for example, to account for a reference that Applicants may be unaware of at the time of the filing of the application.

The term "substituted" when used to describe a group, for example, when referring to a substituted analog of a particular group, is intended to describe any non-hydrogen moiety that formally replaces a hydrogen atom in that group, and is intended to be non-limiting. A group or groups can also be referred to herein as "unsubstituted" or by equivalent terms such as "non-substituted," which refers to the original group in which a non-hydrogen moiety does not replace a hydrogen atom within that group. Unless otherwise specified, "substituted" is intended to be non-limiting and include inorganic substituents or organic substituents as understood by one of ordinary skill in the art.

As used herein, the term "hydrocarbon" refers to a compound containing only carbon and hydrogen atoms. Other identifiers can be utilized to indicate the presence of particular groups, if any, in the hydrocarbon (e.g., halogenated hydrocarbon indicates that the presence of one or more halogen atoms replacing an equivalent number of hydrogen atoms in the hydrocarbon).

An "aromatic" compound is a compound containing a cyclically conjugated double bond system that follows the Hückel (4n+2) rule and contains (4n+2) pi-electrons, where n is an integer from 1 to 5. Aromatic compounds include "arenes" (hydrocarbon aromatic compounds, e.g., benzene, toluene, xylene, etc.) and "heteroarenes" (heteroaromatic compounds formally derived from arenes by replacement of one or more methine (—C═) carbon atoms of the cyclically conjugated double bond system with a trivalent or divalent heteroatoms, in such a way as to maintain the continuous pi-electron system characteristic of an aromatic system and a number of out-of-plane pi-electrons corresponding to the Hückel rule (4n+2)). As disclosed herein, the term "substituted" can be used to describe an aromatic group, arene, or heteroarene, wherein a non-hydrogen moiety formally replaces a hydrogen atom in the compound, and is intended to be non-limiting, unless specified otherwise.

As used herein, the term "alkane" refers to a saturated hydrocarbon compound. Other identifiers can be utilized to indicate the presence of particular groups, if any, in the alkane (e.g., halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. The alkane or alkyl group can be linear or branched unless otherwise specified.

A "cycloalkane" is a saturated cyclic hydrocarbon, with or without side chains, for example, cyclobutane, cyclopentane, cyclohexane, methyl cyclopentane, methyl cyclohexane, etc. Other identifiers can be utilized to indicate the presence of particular groups, if any, in the cycloalkane (e.g., halogenated cycloalkane indicates that the presence of one or more halogen atoms replacing an equivalent number of hydrogen atoms in the cycloalkane).

The term "halogen" has its usual meaning. Examples of halogens include fluorine, chlorine, bromine, and iodine.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

DETAILED DESCRIPTION OF THE INVENTION

Disclosed herein are methods for treating or regenerating a spent catalyst, such as a spent aromatization catalyst. Related reforming processes also are disclosed.

Methods for Treating Spent Catalysts

Various methods for treating or regenerating spent catalysts comprising a transition metal and a catalyst support are disclosed and described. One such method of treating or regenerating a spent catalyst can comprise (or consist essentially of, or consist of):

(i) contacting the spent catalyst with a halogen-containing stream comprising chlorine and fluorine to produce a halogenated spent catalyst; and (ii) contacting the halogenated spent catalyst with a decoking gas stream comprising oxygen.

Generally, the features of any of the methods disclosed herein (e.g., the spent catalyst, the transition metal, the catalyst support, the halogen-containing stream, the conditions under which the halogenation step is conducted, the decoking gas stream, the conditions under which the decoking step is conducted, among others) are independently described herein, and these features can be combined in any combination to further describe the disclosed methods. Moreover, other process steps can be conducted before, during, and/or after any of the steps listed in the disclosed methods, unless stated otherwise. Additionally, reactivated catalysts produced in accordance with the disclosed methods/processes are within the scope of this disclosure and are encompassed herein.

Step (i) of the method often can be referred to as the halogenation step, and in the halogenation step, a halogen-containing stream comprising chlorine (Cl) and fluorine (F) can be contacted with the spent catalyst. In some embodiments, the molar ratio of Cl:F in the halogen-containing stream can be in a range from about 0.1:1 to about 25:1, while in other embodiments, the molar ratio of Cl:F in the halogen-containing stream can be in a range from about 0.1:1 to about 20:1. Molar ratios of Cl:F in the halogen-containing stream in a range from about 0.1:1 to about 15:1, from about 0.2:1 to about 15:1, from about 0.2:1 to about 10:1, from about 0.2:1 to about 5:1, from about 0.3:1 to about 3:1, from about 0.1:1 to about 1:1, or from about 0.3:1 to about 0.8:1, also can be employed in embodiments contemplated herein.

Any compositional attributes of the halogen-containing stream are meant to refer to the incoming halogen-containing stream, prior to contacting the spent catalyst, unless expressly stated otherwise. As one of skill in the art would readily recognize, the outgoing halogen-containing stream, after contacting the spent catalyst, can vary significantly in composition from the incoming halogen-containing stream.

The sources of chlorine and fluorine in the halogen-containing stream can be varied. For instance, the halogen-containing stream can comprise a chlorine-containing compound and a fluorine-containing compound (e.g., at least two distinct compounds); or a chlorine/fluorine-containing compound (e.g., at least one compound containing both chlorine and fluorine, or a chlorofluorocarbon); or a chlorine-containing compound and a chlorine/fluorine-containing compound; or a chlorine/fluorine-containing compound and a fluorine-containing compound; and so forth.

In an embodiment, suitable chlorine-containing compounds can include, but are not limited to, hydrochloric acid, chlorine gas ($Cl_2$), carbon tetrachloride, tetrachloroethylene, chlorobenzene, methyl chloride, methylene chloride, chloroform, allyl chloride, trichloroethylene, a chloramine, a chlorine oxide, a chlorine acid, chlorine dioxide, dichlorine monoxide, dichlorine heptoxide, chloric acid, perchloric acid, ammonium chloride, tetramethylammonium chloride, tetraethylammonium chloride, tetrapropylammonium chloride, tetrabutylammonium chloride, methyltriethylammonium chloride, and the like, or any combination thereof. Other suitable chlorine-containing compounds can include arenes and alkyl-substituted arenes (e.g., benzene, toluene, xylene, etc.), where at least one hydrogen atom is replaced with a Cl atom.

In another embodiment, the chlorine-containing compound can comprise (or consist essentially of, or consist of) hydrochloric acid; alternatively, chlorine gas ($Cl_2$); alternatively, carbon tetrachloride; alternatively, tetrachloroethylene; alternatively, chlorobenzene; alternatively, methyl chloride; alternatively, methylene chloride; alternatively, chloroform; alternatively, allyl chloride; alternatively, trichloroethylene; alternatively, a chloramine; alternatively, a chlorine oxide; alternatively, a chlorine acid; alternatively, chlorine dioxide; alternatively, dichlorine monoxide; alternatively, dichlorine heptoxide; alternatively, chloric acid; alternatively, perchloric acid; alternatively, ammonium chloride; alternatively, tetramethylammonium chloride; alternatively, tetraethylammonium chloride; alternatively, tetrapropylammonium chloride; alternatively, tetrabutylammonium chloride; or alternatively, methyltriethylammonium chloride.

In an embodiment, suitable fluorine-containing compounds can include, but are not limited to, hydrofluoric acid, fluorine gas ($F_2$), 2,2,2-trifluoroethanol, tetrafluoroethylene, carbon tetrafluoride, carbon trifluoride, fluoromethane, heptafluoropropane, decafluorobutane, hexafluoroisopropanol, tetrafluoropropanol, pentafluoropropanol, hexafluorophenylpropanol, perfluorobutyl alcohol, hexafluor-2-propanol, pentafluoro-1-propanol, tetrafluoro-1-propanol, 1,1,1,3,3,3-hexafluoro-2-propanol, 2,2,3,3,3-pentafluoro-1-propanol, ammonium fluoride, tetramethylammonium fluoride, tetraethylammonium fluoride, tetrapropylammonium fluoride, tetrabutylammonium fluoride, methyltriethylammonium fluoride, and the like, or any combination thereof. Other suitable fluorine-containing compounds can include arenes and alkyl-substituted arenes (e.g., benzene, toluene, xylene, etc.), where at least one hydrogen atom is replaced with a F atom.

In another embodiment, the fluorine-containing compound can comprise (or consist essentially of, or consist of) hydrofluoric acid; alternatively, fluorine gas ($F_2$); alternatively, 2,2,2-trifluoroethanol; alternatively, tetrafluoroethylene; alternatively, carbon tetrafluoride; alternatively, carbon trifluoride; alternatively, fluoromethane; alternatively, heptafluoropropane; alternatively, decafluorobutane; alternatively, hexafluoroisopropanol; alternatively, tetrafluoropropanol; alternatively, pentafluoropropanol; alternatively, hexafluorophenylpropanol; alternatively, perfluorobutyl alcohol; alternatively, hexafluor-2-propanol; alternatively, pentafluoro-1-propanol; alternatively, tetrafluoro-1-propanol; alternatively, 1,1,1,3,3,3-hexafluoro-2-propanol; alternatively, 2,2,3,3,3-pentafluoro-1-propanol; alternatively, ammonium fluoride; alternatively, tetramethylammonium fluoride; alternatively, tetraethylammonium fluoride; alternatively, tetrapropylammonium fluoride; alternatively, tetrabutylammonium fluoride; or alternatively, methyltriethylammonium fluoride.

Suitable chlorine/fluorine-containing compounds (or chlorofluorocarbons) can include, but are not limited to, $CF_3Cl$, $CF_2Cl_2$, $CFCl_3$, $CHFCl_2$, $CHF_2Cl$, $C_2F_2Cl_4$, $C_2F_4Cl_2$, and the like, or any combination thereof. Thus, the halogen-containing stream can comprise (or consist essentially of, or consist of) a chlorine/fluorine-containing compound or chlorofluorocarbon in certain embodiments.

In addition to chlorine and fluorine, the halogen-containing stream can further comprise an inert gas, such as helium, neon, argon, or nitrogen, or combinations of two or more of these materials. In certain embodiments, the halogen-containing stream can comprise (or consist essentially of, or consist of) chlorine, fluorine, and an inert gas, and the inert gas can be or can comprise nitrogen. In a further embodiment, the halogen-containing stream can comprise (or consist essentially of, or consist of) chlorine gas ($Cl_2$), fluorine gas ($F_2$), and nitrogen.

In certain embodiments, the amount of chlorine (Cl) and fluorine (F), individually, in the halogen-containing stream can be less than about 5% by volume. For instance, the halogen-containing stream can comprise a concentration in ppmv (ppm by volume) of Cl of less than about 25,000 and/or a ppmv of F of less than about 25,000; alternatively, a ppmv of Cl of less than about 10,000 and/or a ppmv of F of less than about 10,000; alternatively, a ppmv of Cl of less than about 5,000 and/or a ppmv of F of less than about 5,000; alternatively, a ppmv of Cl of less than about 2,500 and/or a ppmv of F of less than about 2,500. Suitable ranges of the concentration of Cl and/or F can include, but are not limited to, the following ranges: from about 50 to about 25,000 ppmv, from about 50 to about 5,000 ppmv, from about 50 to about 2,500 ppmv, from about 50 to about 1,000 ppmv, from about 250 to about 25,000 ppmv, from about 250 to about 10,000 ppmv, from about 250 to about 5,000 ppmv, from about 250 to about 2,000 ppmv, from about 500 to about 5,000 ppmv, from about 500 to about 2,500 ppmv, and the like.

Additionally, or alternatively, the halogen-containing stream can be substantially free of oxygen-containing compounds, such as oxygen ($O_2$), water ($H_2O$), etc. As used herein, "substantially free" of oxygen-containing compounds means less than 100 ppmw (ppm by weight) of oxygen-containing compounds in the halogen-containing stream. Therefore, it is contemplated that the amount of oxygen-containing compounds in the halogen-containing stream can be less than 50 ppmw, less than 25 ppmw, less than 10 ppmw, less than 5 ppmw, or less than 3 ppmw, in certain embodiments. In other embodiments, the amount of oxygen-containing compounds in the halogen-containing stream can be in range from about 0.1 to 100 ppmw, from about 0.5 to 100 ppmw, from about 1 to 100 ppmw, from about 0.1 to about 50 ppmw, from about 0.1 to about 25 ppmw, from about 0.1 to about 10 ppmw, or from about 0.1 to about 5 ppmw. While not wishing to be bound by theory, Applicants believe that it can be beneficial to have substantially no oxygen added during the halogenation step of the method of treating a spent catalyst.

The halogenation step can be conducted at a variety of temperatures and time periods. For instance, the halogenation step can be conducted at a halogenation temperature in a range from about 0° C. to about 500° C.; alternatively, from about 100° C. to about 500° C.; alternatively, from about 0° C. to about 400° C.; alternatively, from about 100° C. to about 450° C.; alternatively, from about 150° C. to about 350° C.; alternatively, from about 20° C. to about 350° C.; alternatively, from about 25° C. to about 300° C.; alternatively, from about 25° C. to about 250° C.; alternatively, from about 50° C. to about 280° C.; alternatively, from about 120° C. to about 320° C.; alternatively, from about 150° C. to about 300° C.; alternatively, from about 150° C. to about 280° C.; or alternatively, from about 170° C. to about 250° C. In these and other embodiments, these temperature ranges also are meant to encompass circumstances where the halogenation step is conducted at a series of different temperatures, instead of at a single fixed temperature, falling within the respective ranges.

The duration of the halogenation step is not limited to any particular period of time. Hence, the halogenation step can be conducted, for example, in a time period ranging from as little as 30-45 minutes to as long as 12-24 hours, 36-48 hours, or more. The appropriate halogenation time can depend upon, for example, the halogenation temperature, and the amounts of chlorine and fluorine in the halogen-containing stream, among other variables. Generally, however, the halogenation step can be conducted in a time period that can be in a range from about 45 minutes to about 48 hours, such as, for example, from about 1 hour to about 48 hours, from about 45 minutes to about 24 hours, from about 45 minutes to about 18 hours, from about 1 hour to about 12 hours, from about 2 hours to about 12 hours, from about 4 hours to about 10 hours, or from about 2 hours to about 8 hours.

Other methods for treating or regenerating spent catalysts comprising a transition metal and a catalyst support also are disclosed and described herein. In one embodiment, the method of treating or regenerating a spent catalyst can comprise (or consist essentially of, or consist of):

(1) contacting the spent catalyst with a fluorine-containing stream comprising a fluorine-containing compound to produce a fluorinated spent catalyst;

(2) contacting the fluorinated spent catalyst with a chlorine-containing stream comprising a chlorine-containing compound to produce a fluorinated-chlorinated spent catalyst; and (3) contacting the fluorinated-chlorinated spent catalyst with a decoking gas stream comprising oxygen.

In another embodiment, the method of treating or regenerating a spent catalyst can comprise (or consist essentially of, or consist of):

(1) contacting the spent catalyst with a chlorine-containing stream comprising a chlorine-containing compound to produce a chlorinated spent catalyst;

(2) contacting the chlorinated spent catalyst with a fluorine-containing stream comprising a fluorine-containing compound to produce a chlorinated-fluorinated spent catalyst; and (3) contacting the chlorinated-fluorinated spent catalyst with a decoking gas stream comprising oxygen.

Generally, the features of any of the methods disclosed herein (e.g., the spent catalyst, the transition metal, the catalyst support, the fluorine-containing stream, the chlorine-containing stream, the conditions under which the fluorination step is conducted, the conditions under which the chlorination step is conducted, the decoking gas stream, the conditions under which the decoking step is conducted, among others) are independently described herein, and these features can be combined in any combination to further describe the disclosed methods. Moreover, other process steps can be conducted before, during, and/or after any of the steps listed in the disclosed methods, unless stated otherwise. Additionally, reactivated catalysts produced in accordance with the disclosed methods/processes are within the scope of this disclosure and are encompassed herein.

The steps of these methods that utilize a fluorine-containing stream often can be referred to as fluorination steps, while the steps of these methods that utilize a chlorine-containing stream often can be referred to as chlorination steps. Any compositional attributes of the fluorine-containing stream and the chlorine-containing stream are meant to refer to the respective incoming fluorine-containing stream and chlorine-containing stream, prior to contacting the spent catalyst, unless expressly stated otherwise. As one of skill in the art would readily recognize, the outgoing fluorine-containing stream and chlorine-containing stream, after contacting the spent catalyst, can vary significantly in composition from the respective incoming fluorine-containing stream and chlorine-containing stream.

The fluorine-containing compound in the fluorine-containing stream can be any fluorine-containing compound disclosed herein as being suitable as a fluorine-containing compound in the halogen-containing stream. For instance, the fluorine-containing compound can comprise (or consist essentially of, or consist of) fluorine gas ($F_2$). In addition to fluorine, the fluorine-containing stream can further comprise an inert gas, such as helium, neon, argon, or nitrogen, or combinations of two or more of these materials. In certain embodiments, the fluorine-containing stream can comprise (or consist essentially of, or consist of) a fluorine-containing compound and an inert gas, and the inert gas can be or can comprise nitrogen. In a further embodiment, the fluorine-containing stream can comprise (or consist essentially of, or consist of) fluorine gas ($F_2$) and nitrogen.

In certain embodiments, the amount of fluorine (F) in the fluorine-containing stream can be less than about 5% by volume. For instance, the fluorine-containing stream can comprise a concentration in ppmv (ppm by volume) of F of less than about 25,000; alternatively, a ppmv of F of less than about 10,000; alternatively, a ppmv of F of less than about 5,000; alternatively, a ppmv of F of less than about 2,500. Suitable ranges of the concentration of F can include, but are not limited to, the following ranges: from about 50 to about 25,000 ppmv, from about 50 to about 5,000 ppmv, from about 50 to about 2,500 ppmv, from about 50 to about 1,000 ppmv, from about 250 to about 25,000 ppmv, from about 250 to about 10,000 ppmv, from about 250 to about 5,000 ppmv, from about 250 to about 2,000 ppmv, from about 500 to about 5,000 ppmv, from about 500 to about 2,500 ppmv, and the like.

The fluorine-containing stream can be substantially free of oxygen-containing compounds (e.g., oxygen ($O_2$), water ($H_2O$), etc.), i.e., can contain less than 100 ppmw (ppm by weight) of oxygen-containing compounds. Therefore, it is contemplated that the amount of oxygen-containing compounds in the fluorine-containing stream can be less than 50 ppmw, less than 25 ppmw, less than 10 ppmw, less than 5 ppmw, or less than 3 ppmw, in certain embodiments. In other embodiments, the amount of oxygen-containing compounds in the fluorine-containing stream can be in range from about 0.1 to 100 ppmw, from about 0.5 to 100 ppmw, from about 1 to 100 ppmw, from about 0.1 to about 50 ppmw, from about 0.1 to about 25 ppmw, from about 0.1 to about 10 ppmw, or from about 0.1 to about 5 ppmw. While not wishing to be bound by theory, Applicants believe that it can be beneficial to have substantially no oxygen added during the fluorination step of the method of treating a spent catalyst. Moreover, although not required, the fluorine-containing stream can be substantially free of chlorine-containing compounds, i.e., can contain less than 100 ppmw (ppm by weight) of chlorine-containing compounds. As above, it is contemplated that the amount of chlorine-containing compounds in the fluorine-containing stream can be, for instance, less than 50 ppmw, less than 10 ppmw, in a range from about 0.1 to 100 ppmw, in a range from about 0.1 to about 50 ppmw, or in a range from about 0.1 to about 10 ppmw, and the like.

The fluorination step can be conducted at a variety of temperatures and time periods. For instance, the fluorination step can be conducted at a fluorination temperature in a range from about 0° C. to about 500° C.; alternatively, from about 100° C. to about 500° C.; alternatively, from about 0° C. to about 400° C.; alternatively, from about 100° C. to about 450° C.; alternatively, from about 150° C. to about 350° C.; alternatively, from about 20° C. to about 350° C.; alternatively, from about 25° C. to about 300° C.; alternatively, from about 25° C. to about 250° C.; alternatively, from about 10° C. to about 100° C.; alternatively, from about 20° C. to about 50° C.; alternatively, from about 50° C. to about 280° C.; alternatively, from about 120° C. to about 320° C.; alternatively, from about 150° C. to about 300° C.; alternatively, from about 150° C. to about 280° C.; or alternatively, from about 170° C. to about 250° C. In these and other embodiments, these temperature ranges also are meant to encompass circumstances where the fluorination step is conducted at a series of different temperatures, instead of at a single fixed temperature, falling within the respective ranges.

The duration of the fluorination step is not limited to any particular period of time. Hence, the fluorination step can be conducted, for example, in a time period ranging from as little as 30-45 minutes to as long as 12-24 hours, 36-48 hours, or more. The appropriate fluorination time can depend upon, for example, the fluorination temperature, and the amount of fluorine in the fluorine-containing stream, among other variables. Generally, however, the fluorination step can be conducted in a time period that can be in a range from about 45 minutes to about 48 hours, such as, for example, from about 1 hour to about 48 hours, from about 45 minutes to about 24 hours, from about 45 minutes to about 18 hours, from about 1 hour to about 12 hours, from about 2 hours to about 12 hours, from about 4 hours to about 10 hours, or from about 2 hours to about 8 hours.

The chlorine-containing compound in the chlorine-containing stream can be any chlorine-containing compound disclosed herein as being suitable as a chlorine-containing compound in the halogen-containing stream. For instance, the chlorine-containing compound can comprise (or consist essentially of, or consist of) chlorine gas ($Cl_2$). In addition to chlorine, the chlorine-containing stream can further comprise an inert gas, such as helium, neon, argon, or nitrogen, or combinations of two or more of these materials. In certain embodiments, the chlorine-containing stream can comprise (or consist essentially of, or consist of) a chlorine-containing compound and an inert gas, and the inert gas can be or can comprise nitrogen. In a further embodiment, the chlorine-containing stream can comprise (or consist essentially of, or consist of) chlorine gas ($Cl_2$) and nitrogen.

In certain embodiments, the amount of chlorine (Cl) in the chlorine-containing stream can be less than about 5% by volume. For instance, the chlorine-containing stream can comprise a concentration in ppmv (ppm by volume) of Cl of less than about 25,000; alternatively, a ppmv of Cl of less than about 10,000; alternatively, a ppmv of Cl of less than about 5,000; alternatively, a ppmv of Cl of less than about 2,500. Suitable ranges of the concentration of Cl can include, but are not limited to, the following ranges: from about 50 to about 25,000 ppmv, from about 50 to about 5,000 ppmv, from about 50 to about 2,500 ppmv, from about 50 to about 1,000 ppmv, from about 250 to about 25,000 ppmv, from about 250 to about 10,000 ppmv, from about 250 to about 5,000 ppmv, from about 250 to about 2,000 ppmv, from about 500 to about 5,000 ppmv, from about 500 to about 2,500 ppmv, and the like.

The chlorine-containing stream can be substantially free of oxygen-containing compounds (e.g., oxygen ($O_2$), water ($H_2O$), etc.), i.e., can contain less than 100 ppmw (ppm by weight) of oxygen-containing compounds. Therefore, it is contemplated that the amount of oxygen-containing compounds in the chlorine-containing stream can be less than 50 ppmw, less than 25 ppmw, less than 10 ppmw, less than 5 ppmw, or less than 3 ppmw, in certain embodiments. In other embodiments, the amount of oxygen-containing compounds in the chlorine-containing stream can be in range from about 0.1 to 100 ppmw, from about 0.5 to 100 ppmw, from about 1 to 100 ppmw, from about 0.1 to about 50 ppmw, from about 0.1 to about 25 ppmw, from about 0.1 to about 10 ppmw, or from about 0.1 to about 5 ppmw. While not wishing to be bound by theory, Applicants believe that it can be beneficial to have substantially no oxygen added during the chlorination step of the method of treating a spent catalyst. Moreover, although not required, the chlorine-containing stream can be substantially free of fluorine-containing compounds, i.e., can contain less than 100 ppmw (ppm by weight) of fluorine-containing compounds. As above, it is contemplated that the amount of fluorine-containing compounds in the chlorine-containing stream can be, for instance, less than 50 ppmw, less than 10 ppmw, in a range from about 0.1 to 100 ppmw, in a range from about 0.1 to about 50 ppmw, or in a range from about 0.1 to about 10 ppmw, and the like.

The chlorination step can be conducted at a variety of temperatures and time periods. For instance, the chlorination step can be conducted at a chlorination temperature in a range from about 0° C. to about 500° C.; alternatively, from about 100° C. to about 500° C.; alternatively, from about 0° C. to about 400° C.; alternatively, from about 100° C. to about 450° C.; alternatively, from about 150° C. to about 350° C.; alternatively, from about 20° C. to about 350° C.; alternatively, from about 25° C. to about 300° C.; alternatively, from about 25° C. to about 250° C.; alternatively, from about 10° C. to about 100° C.; alternatively, from about 20° C. to about 50° C.; alternatively, from about 50° C. to about 280° C.; alternatively, from about 120° C. to about 320° C.; alternatively, from about 150° C. to about 300° C.; alternatively, from about 150° C. to about 280° C.; or alternatively, from about 170° C. to about 250° C. In these and other embodiments, these temperature ranges also are meant to encompass circumstances where the chlorination step is conducted at a series of different temperatures, instead of at a single fixed temperature, falling within the respective ranges.

The duration of the chlorination step is not limited to any particular period of time. Hence, the chlorination step can be conducted, for example, in a time period ranging from as little as 30-45 minutes to as long as 12-24 hours, 36-48 hours, or more. The appropriate chlorination time can depend upon, for example, the chlorination temperature, and the amount of chlorine in the chlorine-containing stream, among other variables. Generally, however, the chlorination step can be conducted in a time period that can be in a range from about 45 minutes to about 48 hours, such as, for example, from about 1 hour to about 48 hours, from about 45 minutes to about 24 hours, from about 45 minutes to about 18 hours, from about 1 hour to about 12 hours, from about 2 hours to about 12 hours, from about 4 hours to about 10 hours, or from about 2 hours to about 8 hours.

In various embodiments contemplated herein, the methods of treating or regenerating a spent catalyst can further include an optional halogen purge step prior to the carbon burn step, and between the fluorination and chlorination step or between the chlorination and fluorination step. In one embodiment, for example, a method of treating or regenerating a spent catalyst (e.g., comprising a transition metal and a catalyst support) comprising a fluorination step, followed by a chlorination step and a carbon burn step, can further comprise a halogen purge step prior to the chlorination step. This halogen purge step can comprise contacting the fluorinated spent catalyst with a halogen purge stream comprising (or consisting essentially of, or consisting of) an inert gas. In another embodiment, a method of treating or regenerating a spent catalyst (e.g., comprising a transition metal and a catalyst support) comprising a chlorination step, followed by a fluorination step and a carbon burn step, can further comprise a halogen purge step prior to the fluorination step. This halogen purge step can comprise contacting the chlorinated spent catalyst with a halogen purge stream comprising (or consisting essentially of, or consisting of) an inert gas. In these halogen purge steps, the inert gas can be helium, neon, argon, or nitrogen, or a mixture thereof; alternatively, helium; alternatively, neon; alternatively, argon; or alternatively, nitrogen.

In some embodiments, the halogen purge stream can be substantially free of oxygen-containing compounds (e.g., oxygen, water, etc.), as discussed above in relation to the halogenation step. Hence, the halogen purge step can be conducted in the presence of less than 100 ppmw of oxygen-containing compounds, or less than 50 ppmw, or less than 25 ppmw, or less than 10 ppmw, or less than 5 ppmw, or less than 3 ppmw.

Additionally, in some embodiments, the halogen purge stream can be substantially free of halogen-containing compounds, as discussed herein in relation to the carbon burn step. Hence, the halogen purge step can be conducted in the presence of less than 100 ppmw of halogen-containing compounds, or less than 50 ppmw, or less than 25 ppmw, or less than 10 ppmw, or less than 5 ppmw, or less than 3 ppmw.

The halogen purge step can be performed at a halogen purge temperature which generally can encompass the same temperature range as the halogenation temperature used in the halogenation step. Accordingly, the halogen purge temperature can be in a range from about 0° C. to about 500° C.; alternatively, from about 100° C. to about 500° C.; alternatively, from about 0° C. to about 400° C.; alternatively, from about 100° C. to about 400° C.; alternatively, from about 150° C. to about 400° C.; alternatively, from about 20° C. to about 350° C.; alternatively, from about 25° C. to about 300° C.; alternatively, from about 180° C. to about 320° C.; alternatively, from about 180° C. to about 280° C.; or alternatively, from about 200° C. to about 300° C. In these and other embodiments, these temperature ranges also are meant to encompass circumstances where the halogen purge step is conducted at a series of different temperatures, instead of at a single fixed temperature, falling within the respective ranges.

The duration of the halogen purge step is not limited to any particular period of time. Typically, the halogen purge step can be conducted in a time period ranging from as little as 30-45 minutes to as long as 48-72 hours (or more), but more typically, the purging step can be conducted in a time period that can be in a range from about 1 hour to about 48 hours, such as, for example, from about 1 hour to about 36 hours, from about 2 hours to about 36 hours, from about 2 hours to about 24 hours, or from about 2 hours to about 18 hours.

Alternatively, the halogen purge step can be conducted for a time period sufficient to reduce the halogen content of the outgoing purging stream, after contacting the spent catalyst (the fluorinated spent catalyst or the chlorinated spent catalyst), to less than 100 ppmw of halogen-containing compounds (i.e., substantially halogen-free). For instance, after contacting the spent catalyst with a fluorine-containing stream comprising a fluorine-containing compound to produce a fluorinated spent catalyst, the halogen purge step can be conducted for a time period sufficient to reduce the fluorine content of the outgoing halogen purge stream, after contacting the fluorinated spent catalyst, to less than about 100 ppmw of fluorine-containing compounds; alternatively, less than about 50 ppmw; alternatively, less than about 25 ppmw; alternatively, less than about 10 ppmw; alternatively, less than about 5 ppmw; or alternatively, less than about 3 ppmw. Likewise, after contacting the spent catalyst with a chlorine-containing stream comprising a chlorine-containing compound to produce a chlorinated spent catalyst, the halogen purge step can be conducted for a time period sufficient to reduce the chlorine content of the outgoing halogen purge stream, after contacting the chlorinated spent catalyst, to less than about 100 ppmw of chlorine-containing compounds; alternatively, less than about 50 ppmw; alternatively, less than about 25 ppmw; alternatively, less than about 10 ppmw; alternatively, less than about 5 ppmw; or alternatively, less than about 3 ppmw.

Step (ii) and step (3) of the method for treating or regenerating a spent catalyst often can be referred to as the carbon burn step, or decoking step, and in this step, a halogenated spent catalyst (or a fluorinated-chlorinated spent catalyst, or a chlorinated-fluorinated spent catalyst) can be contacted with a decoking gas stream comprising oxygen. In addition to oxygen, the decoking gas stream can comprise an inert gas, i.e., the decoking gas stream can comprise (or consist essentially of, or consist of) oxygen and an inert gas. Typical inert gasses useful in the carbon burn step can encompass helium, neon, argon, nitrogen, and the like, and this includes combinations of two or more of these materials. In certain embodiments, the decoking gas stream can comprise (or consist essentially of, or consist of) oxygen and nitrogen; alternatively, air and nitrogen; or alternatively, air.

Since the decoking gas stream can comprise air, the decoking gas stream can comprise about 20-21 mole % oxygen. More often, however, the amount of oxygen in the decoking gas can be less than about 10 mole %. For example, in some embodiments, the decoking gas stream can comprise less than about 8 mole %, less than about 5 mole %, or less than about 3 mole % oxygen. Accordingly, suitable ranges for the mole % of oxygen in the decoking gas stream can include, but are not limited to, the following ranges: from about 0.1 to about 25 mole %, from about 0.1 to about 20 mole %, from about 0.2 to about 10 mole %, from about 0.2 to about 5 mole %, from about 0.3 to about 5 mole %, from about 0.5 to about 5 mole %, from about 0.5 to about 4 mole %, from about 0.5 to about 3 mole %, or from about 1 to about 3 mole %, and the like.

In an embodiment, the decoking gas stream can be substantially halogen-free, i.e., substantially free of halogen-containing compounds. In this context, "substantially halogen-free" means less than 100 ppmw (ppm by weight) of halogen-containing compounds in the decoking gas stream. Therefore, it is contemplated that the amount of halogen-containing compounds in the decoking gas stream can be less than 50 ppmw, less than 25 ppmw, less than 10 ppmw, less than 5 ppmw, or less than 3 ppmw, in certain embodiments. In other embodiments, the amount of halogen-containing compounds in the decoking gas stream can be in range from about 0.1 to 100 ppmw, from about 0.5 to 100 ppmw, from about 1 to 100 ppmw, from about 0.1 to about 50 ppmw, from about 0.1 to about 25 ppmw, from about 0.1 to about 10 ppmw, or from about 0.1 to about 5 ppmw. While not wishing to be bound by theory, Applicants believe that it can be beneficial to have substantially no halogens added during the carbon burn step of the method of treating a spent catalyst.

In another embodiment, the decoking gas stream can be substantially free of water, and in this regard, "substantially free" means less than 100 ppmw (ppm by weight) of water in the decoking gas stream. Therefore, it is contemplated that the amount of water in the decoking gas stream can be less than 50 ppmw, less than 25 ppmw, less than 10 ppmw, less than 5 ppmw, or less than 3 ppmw, in certain embodiments. In other embodiments, the amount of water in the decoking gas stream can be in range from about 0.1 to 100 ppmw, from about 0.5 to 100 ppmw, from about 1 to 100 ppmw, from about 0.1 to about 50 ppmw, from about 0.1 to about 25 ppmw, from about 0.1 to about 10 ppmw, or from about 0.1 to about 5 ppmw. While not wishing to be bound by theory, Applicants believe that it can be beneficial to have substantially no water added during the carbon burn step of the method of treating a spent catalyst.

Similar to that described above for the halogen-containing stream, any compositional attributes of the decoking gas stream are meant to refer to the incoming decoking gas stream, prior to contacting the halogenated spent catalyst (or the fluorinated-chlorinated spent catalyst, or the chlorinated-fluorinated spent catalyst), unless expressly stated otherwise. As one of skill in the art would readily recognize, the outgoing decoking gas stream, after contacting the halogenated spent catalyst (or the fluorinated-chlorinated spent catalyst, or the chlorinated-fluorinated spent catalyst), can vary significantly in composition from the incoming decoking gas stream. For instance, halogens deposited during the halogenation step (or fluorination and/or chlorination steps) can elute, in some circumstances, from the catalyst during the carbon burn step. Moreover, water can be produced during the carbon burn step, and thus, water may be detected in the outgoing decoking stream.

The carbon burn step can be conducted at a variety of temperatures and time periods. For instance, the carbon burn step can be conducted at a peak decoking temperature in a range from about 300° C. to about 600° C.; alternatively, from about 300° C. to about 550° C.; alternatively, from about 300° C. to about 500° C.; alternatively, from about 320° C. to about 480° C.; alternatively, from about 340° C. to about 460° C.; or alternatively, from about 350° C. to about 450° C. In these and other embodiments, these temperature ranges also are meant to encompass circumstances where the carbon burn step is conducted at a series of different temperatures (e.g., an initial decoking temperature, a peak decoking temperature), instead of at a single fixed temperature, falling within the respective ranges. For instance, the carbon burn step can start at an initial decoking temperature which is the same as the halogenation temperature in the halogenation step (or fluorination temperature in the fluorination step, or chlorination temperature in the chlorination step). Thus, for example, the carbon burn step can commence at an initial decoking temperature in a range from about 25° C. to about 250° C., from about 10° C. to about 100° C., or from about 50° C. to about 280° C. Subsequently, the temperature of the carbon burn step can be increased to a peak decoking temperature, for example, in a range from about 300° C. to about 600° C., or from about 350° C. to about 450° C.

The duration of the carbon burn step is not limited to any particular period of time. Hence, the carbon burn step can be conducted, for example, in a time period ranging from as little as 30-45 minutes to as long as 48-72 hours, or more. The appropriate decoking time can depend upon, for example, the initial/peak decoking temperature, and the amount of oxygen in the decoking gas stream, among other variables. Generally, however, the carbon burn step can be conducted in a time period that can be in a range from about 45 minutes to about 72 hours, such as, for example, from about 45 minutes to about 48 hours, from about 1 hour to about 48 hours, from about 1 hour to about 12 hours, or from about 1 hour to about 6 hours.

Alternatively, the carbon burn step can be conducted for a time period sufficient to reduce the wt. % of carbon on the halogenated spent catalyst (or the fluorinated-chlorinated spent catalyst, or the chlorinated-fluorinated spent catalyst) to less than about 1 wt. %. In some embodiments, the carbon burn step can be conducted for a time period sufficient to reduce the wt. % of carbon on the halogenated spent catalyst (or the fluorinated-chlorinated spent catalyst, or the chlorinated-fluorinated spent catalyst) to less than about 0.75 wt. %, less than about 0.5 wt. %, or less than about 0.25 wt. %. In other embodiments, the carbon burn step can be conducted for a time period determined by monitoring the $CO_2$ level in the outgoing or exiting decoking stream, after contacting the catalyst. Hence, the carbon burn step can be conducted for a time period sufficient to reduce the amount of $CO_2$ in the outgoing or exiting decoking stream, after contacting the catalyst, to less than about 100 ppmv, for example, less than about 50 ppmv, or less than about 20 ppmv.

Alternatively, the carbon burn step can be conducted for a time period sufficient to result in a treated spent catalyst having an activity that is from about 50% to about 80% of the activity of the fresh catalyst, for example, from about 50% to about 75%, or from about 55% to about 75%. In this regard, the activity of the treated spent catalyst is based on returning to within about 50%-80% of fresh catalyst activity of the same production run of catalyst, tested on the same equipment and under the same method and conditions.

In various embodiments contemplated herein, the methods of treating or regenerating a spent catalyst can further include one or more optional steps performed prior to the halogenation step (or prior to the fluorination and chlorination steps, or prior to the chlorination and fluorination steps) and the carbon burn step. For example, a method of treating or regenerating a spent catalyst can further comprise a partial decoking step prior to the halogenation (or fluorination, or chlorination) step, and/or can further comprise a pre-drying step prior to the halogenation (or fluorination, or chlorination) step, and/or can further comprise a re-coking pretreatment step prior to the halogenation (or fluorination, or chlorination) step. These optional pre-halogenation (or pre-fluorination, or pre-chlorination) steps are discussed in greater detail herein below. In one embodiment, at least one of these optional steps can be performed in a method of treating or regenerating a spent catalyst, while in another embodiment, two of these optional steps can be performed. However, in yet another embodiment, all three of these optional steps can be performed. The pre-halogenation (or pre-fluorination, or pre-chlorination) steps can be performed in any order, however, in a particular embodiment, the partial decoking step can be performed first, followed by the pre-drying step, and then the re-coking step.

In an embodiment, a method of treating or regenerating a spent catalyst (e.g., comprising a transition metal and a catalyst support) comprising a halogenation step (or a fluorination step followed a chlorination step, or a chlorination step followed by a fluorination step) and a carbon burn step can further comprise a partial decoking step prior to the halogenation (or fluorination, or chlorination) step. This partial decoking step generally can comprise contacting the spent catalyst with a partial decoking gas stream comprising oxygen.

The composition of the partial decoking gas stream can encompass the same potential attributes as that described above for the decoking gas stream employed in the carbon burn step. Thus, in addition to oxygen, the partial decoking gas stream can comprise an inert gas, such as helium, neon, argon, and/or nitrogen. In an embodiment, the partial decoking gas stream can comprise (or consist essentially of, or consist of) oxygen and nitrogen; alternatively, air and nitrogen; or alternatively, air. In another embodiment, the partial decoking gas stream often can comprise, for example, from about 0.1 to about 25 mole % oxygen, from about 0.1 to about 20 mole % oxygen, from about 0.2 to about 10 mole % oxygen, from about 0.2 to about 5 mole % oxygen, from about 0.3 to about 5 mole % oxygen, from about 0.5 to about 5 mole % oxygen, from about 0.5 to about 4 mole % oxygen, from about 0.5 to about 3 mole % oxygen, or from about 1 to about 3 mole % oxygen, and the like. In yet another embodiment, the partial decoking gas stream can be substantially halogen-free or substantially free of halogen-containing compounds, i.e., having less than 100 ppmw (ppm by weight) of halogen-containing compounds in the partial decoking gas stream, such as, for example, less than 50 ppmw, less than 25 ppmw, less than 10 ppmw, less than 5 ppmw, or less than 3 ppmw, of halogen-containing compounds in the partial decoking gas stream. In still another embodiment, the partial decoking gas stream can be substantially free of water, i.e., having less than 100 ppmw of water in the partial decoking gas stream, such as, for example, less than 50 ppmw, less than 25 ppmw, less than 10 ppmw, less than 5 ppmw, or less than 3 ppmw, of water in the partial decoking gas stream.

The partial decoking step differs from the carbon burn step in that it can be conducted at a much lower temperature. Generally, the partial decoking step can be conducted at a partial decoking temperature in a range from about from about 125° C. to about 260° C.; alternatively, from about 150° C. to about 250° C.; alternatively, from about 150° C. to about 250° C.; alternatively, from about 175° C. to about 250° C.; alternatively, from about 150° C. to about 225° C.; or alternatively, from about 175° C. to about 225° C. In these and other embodiments, these temperature ranges also are meant to encompass circumstances where the partial decoking step is conducted at a series of different temperatures, instead of at a single fixed temperature, falling within the respective ranges.

The duration of the partial decoking step is not limited to any particular period of time. Typically, the partial decoking step can be conducted in a time period ranging from as little as 30-45 minutes to as long as 48 hours (or more), but more typically, the partial decoking step can be conducted in a time period that can be in a range from about 1 hour to about 36 hours, such as, for example, from about 2 hours to about 36 hours, from about 1 hour to about 24 hours, from about 1 hour to about 18 hours, or from about 2 hours to about 24 hours.

Alternatively, the partial decoking step can be conducted for a time period sufficient to reduce the wt. % of carbon on the spent catalyst to within a range from about 1 to about 10 wt. %, such as, for example, from about 2 to about 10 wt. %, from about 2 to about 8 wt. %, from about 3 to about 7 wt. %, from about 3 to about 6 wt. %, or from about 4 to about 5 wt. % carbon. While not wishing to be bound by theory, Applicants believe that operational health and safety benefits can be achieved by removing liquid hydrocarbons and light oligomers prior to treating the spent catalyst or opening the reactor.

In an embodiment, a method of treating or regenerating a spent catalyst (e.g., comprising a transition metal and a catalyst support) comprising a halogenation step (or a fluorination step followed a chlorination step, or a chlorination step followed by a fluorination step) and a carbon burn step can further comprise a pre-drying step prior to the halogenation (or fluorination, or chlorination) step. This pre-drying step generally can comprise contacting the spent catalyst with a pre-drying gas stream comprising (or consisting essentially of, or consisting of) an inert gas. The inert gas can be helium, neon, argon, or nitrogen, or a mixture thereof; alternatively, helium; alternatively, neon; alternatively, argon; or alternatively, nitrogen. Additionally, in some embodiments, the pre-drying gas stream can be substantially free of oxygen-containing compounds (e.g., oxygen, water, etc), as discussed above in relation to the halogenation step. Hence, the pre-drying step can be conducted in the presence of less than 100 ppmw of oxygen-containing compounds, or less than 50 ppmw, or less than 25 ppmw, or less than 10 ppmw, or less than 5 ppmw, or less than 3 ppmw.

The pre-drying step can be performed at a pre-drying temperature which generally can encompass the same temperature range as the halogenation temperature used in the halogenation step. Accordingly, the pre-drying temperature can be in a range from about 0° C. to about 500° C.; alternatively, from about 100° C. to about 500° C.; alternatively, from about 0° C. to about 400° C.; alternatively, from about 100° C. to about 400° C.; alternatively, from about 150° C. to about 400° C.; alternatively, from about 20° C. to about 350° C.; alternatively, from about 25° C. to about 300° C.; alternatively, from about 150° C. to about 350° C.; alternatively, from about 180° C. to about 320° C.; alternatively, from about 180° C. to about 280° C.; or alternatively, from about 200° C. to about 300° C.

In these and other embodiments, these temperature ranges also are meant to encompass circumstances where the pre-drying step is conducted at a series of different temperatures, instead of at a single fixed temperature, falling within the respective ranges.

The duration of the pre-drying step is not limited to any particular period of time. Typically, the pre-drying step can be conducted in a time period ranging from as little as 30-45 minutes to as long as 48-72 hours (or more), but more typically, the pre-drying step can be conducted in a time period that can be in a range from about 1 hour to about 72 hours, such as, for example, from about 1 hour to about 48 hours, from about 1 hour to about 36 hours, from about 2 hours to about 24 hours, or from about 2 hours to about 18 hours.

Alternatively, the pre-drying step can be conducted for a time period sufficient to reduce the moisture content of the spent catalyst to less than about 4 wt. %, less than about 2 wt. %, less than about 1 wt. %, less than about 0.5 wt. %, or less than about 0.1 wt %.

In an embodiment, a method of treating or regenerating a spent catalyst (e.g., comprising a transition metal and a catalyst support) comprising a halogenation step (or a fluorination step followed a chlorination step, or a chlorination step followed by a fluorination step) and a carbon burn step can further comprise a re-coking pretreatment step prior to the halogenation (or fluorination, or chlorination) step. This re-coking pretreatment step generally can comprise contacting the spent catalyst with a pretreatment stream comprising a hydrocarbon feed and molecular hydrogen. The hydrocarbon feed can be the same as a feed stream to an aromatization process. Thus, in some embodiments, the hydrocarbon feed can comprise $C_6$-$C_8$ alkanes and/or cycloalkanes.

The pretreatment step can be performed at a pretreatment temperature which generally can encompass the same temperature range as the halogenation temperature and/or the temperature used in the aromatization process. Accordingly, the pretreatment temperature can be in a range from about 100° C. to about 600° C.; alternatively, from about 300° C. to about 600° C.; alternatively, from about 400° C. to about 600° C.; alternatively, from about 100° C. to about 350° C.; alternatively, from about 0° C. to about 400° C.; alternatively, from about 20° C. to about 350° C.; alternatively, from about 25° C. to about 300° C.; alternatively, from about 120° C. to about 300° C.; or alternatively, from about 150° C. to about 250° C. In these and other embodiments, these temperature ranges also are meant to encompass circumstances where the pretreatment step is conducted at a series of different temperatures, instead of at a single fixed temperature, falling within the respective ranges.

The duration of the re-coking pretreatment step is not limited to any particular period of time. Typically, the pretreatment step can be conducted in a time period ranging from as little as 30-45 minutes to as long as 48-72 hours (or more), but more typically, the pretreatment step can be conducted in a time period that can be in a range from about 1 hour to about 48 hours, such as, for example, from about 1 hour to about 36 hours, from about 1 hour to about 24 hours, from about 2 hours to about 24 hours, or from about 2 hours to about 18 hours.

Alternatively, the re-coking pretreatment step can be conducted for a time period until the wt. % of carbon on the spent catalyst is within a range from about 1 to about 10 wt. %. Additionally or alternatively, the re-coking pretreatment step can be conducted for a time period sufficient to add from about 0.5 to about 2.5 wt. %, from about 1 to about 2 wt. %, or from about 1 to about 1.5 wt. %, of coke or carbonaceous build-up onto the spent catalyst.

In various embodiments contemplated herein, the methods of treating or regenerating a spent catalyst can further include one or more optional intermediate steps performed after the halogenation step (or after the fluorination and chlorination steps, or after the chlorination and fluorination steps), but prior to the carbon burn step. For example, a method of treating or regenerating a spent catalyst can further comprise a purging step prior to the carbon burn step and/or can further comprise a hydrocarbon treatment step prior to the carbon burn step. These optional intermediate steps are discussed in greater detail herein below. In one embodiment, at least one of these optional intermediate steps can be performed in a method of treating or regenerating a spent catalyst, while in another embodiment, both of these optional intermediate steps can be performed. When both intermediate steps are performed, the intermediate steps can be performed in any order, for example, the halogenation step (or the fluorination and chlorination steps, or the chlorination and fluorination steps), followed by the hydrocarbon treatment step, then the purging step, and then the carbon burn step.

In an embodiment, a method of treating or regenerating a spent catalyst (e.g., comprising a transition metal and a catalyst support) comprising a halogenation step (or a fluorination step followed a chlorination step, or a chlorination step followed by a fluorination step) and a carbon burn step can further comprise a purging step prior to the carbon burn step. This purging step can comprise contacting the halogenated spent catalyst (or the fluorinated-chlorinated spent catalyst, or the chlorinated-fluorinated spent catalyst) with a purging stream comprising (or consisting essentially of, or consisting of) an inert gas. The inert gas can be helium, neon, argon, or nitrogen, or a mixture thereof; alternatively, helium; alternatively, neon; alternatively, argon; or alternatively, nitrogen.

Additionally, in some embodiments, the purging stream can be substantially free of oxygen-containing compounds (e.g., oxygen, water, etc), as discussed above in relation to the halogenation step. Hence, the purging step can be conducted in the presence of less than 100 ppmw of oxygen-containing compounds, or less than 50 ppmw, or less than 25 ppmw, or less than 10 ppmw, or less than 5 ppmw, or less than 3 ppmw.

Additionally, in some embodiments, the purging stream can be substantially free of halogen-containing compounds, as discussed above in relation to the carbon burn step. Hence, the purging step can be conducted in the presence of less than 100 ppmw of halogen-containing compounds, or less than 50 ppmw, or less than 25 ppmw, or less than 10 ppmw, or less than 5 ppmw, or less than 3 ppmw.

The purging step can be performed at a purging temperature which generally can encompass the same temperature range as the halogenation temperature used in the halogenation step. Accordingly, the purging temperature can be in a range from about 0° C. to about 500° C.; alternatively, from about 100° C. to about 500° C.; alternatively, from about 0° C. to about 400° C.; alternatively, from about 100° C. to about 400° C.; alternatively, from about 150° C. to about 400° C.; alternatively, from about 20° C. to about 350° C.; alternatively, from about 25° C. to about 300° C.; alternatively, from about 180° C. to about 320° C.; alternatively, from about 180° C. to about 280° C.; or alternatively, from about 200° C. to about 300° C. In these and other embodiments, these temperature ranges also are meant to encompass circumstances where the purging step is conducted at a series of different temperatures, instead of at a single fixed temperature, falling within the respective ranges.

The duration of the purging step is not limited to any particular period of time. Typically, the purging step can be conducted in a time period ranging from as little as 30-45 minutes to as long as 48-72 hours (or more), but more typically, the purging step can be conducted in a time period that can be in a range from about 1 hour to about 48 hours, such as, for example, from about 1 hour to about 36 hours, from about 2 hours to about 36 hours, from about 2 hours to about 24 hours, or from about 2 hours to about 18 hours.

Alternatively, the purging step can be conducted for a time period sufficient to reduce the halogen content of the outgoing purging stream, after contacting the halogenated spent catalyst (or the fluorinated-chlorinated spent catalyst, or the chlorinated-fluorinated spent catalyst), to less than 100 ppmw of halogen-containing compounds (i.e., substantially halogen-free). In some embodiments consistent with the disclosure herein, the halogen content of the outgoing purging stream, after contacting the halogenated spent catalyst (or the fluorinated-chlorinated spent catalyst, or the chlorinated-fluorinated spent catalyst), can be less than 50 ppmw, less than 25 ppmw, less than 10 ppmw, less than 5 ppmw, or less than 3 ppmw. While not wishing to be bound by theory, Applicants believe that it can be beneficial to have halogens closely associated with the catalyst during the carbon burn step, but substantially no halogens present in the free volume of the atmosphere surrounding the halogenated spent catalyst, or the fluorinated-chlorinated spent catalyst, or the chlorinated-fluorinated spent catalyst (e.g., in the vessel containing the spent catalyst).

In an embodiment, a method of treating or regenerating a spent catalyst (e.g., comprising a transition metal and a catalyst support) comprising a halogenation step (or a fluorination step followed a chlorination step, or a chlorination step followed by a fluorination step) and a carbon burn step can further comprise a hydrocarbon treatment step prior to the carbon burn step. This hydrocarbon treatment step can comprise contacting the halogenated spent catalyst (or the fluorinated-chlorinated spent catalyst, or the chlorinated-fluorinated spent catalyst) with a hydrocarbon treatment stream comprising a hydrocarbon feed. The hydrocarbon treatment stream can be the same as a feed stream to an aromatization process. Hence, in some embodiments, the hydrocarbon treatment stream can comprise $C_6$-$C_8$ alkanes and/or cycloalkanes.

The hydrocarbon treatment step can be performed at a hydrocarbon treatment temperature which generally can encompass the same temperature range as the temperature range used in the aromatization process. In some embodiments, the hydrocarbon treatment temperature can be in a range from about 300° C. to about 600° C.; alternatively, from about 350° C. to about 600° C.; alternatively, from about 400° C. to about 600° C.; alternatively, from about 350° C. to about 550° C.; or alternatively, from about 450° C. to about 550° C. In these and other embodiments, these temperature ranges also are meant to encompass circumstances where the hydrocarbon treatment step is conducted at a series of different temperatures, instead of at a single fixed temperature, falling within the respective ranges.

The duration of the hydrocarbon treatment step is not limited to any particular period of time. Typically, the hydrocarbon treatment step can be conducted in a time period ranging from as little as 30-45 minutes to as long as 48-72 hours (or more), but more typically, the hydrocarbon treatment step can be conducted in a time period that can be in a range from about 1 hour to about 48 hours, such as, for example, from about 1 hour to about 36 hours, from about 1 hour to about 24 hours, from about 2 hours to about 24 hours, or from about 2 hours to about 18 hours.

In various embodiments contemplated herein, the methods of treating or regenerating a spent catalyst can further include one or more optional final steps performed after the carbon burn step. For example, a method of treating or regenerating a spent catalyst can further comprise a reducing step after the carbon burn step. This reducing step can comprise contacting the de-coked catalyst with a reducing gas stream comprising molecular hydrogen. In addition to molecular hydrogen, the reducing gas stream can comprise an inert gas, i.e., the reducing gas stream can comprise (or consist essentially of, or consist of) molecular hydrogen and an inert gas. Typical inert gasses useful in the reducing step can encompass helium, neon, argon, nitrogen, and the like, and this includes combinations of two or more of these materials. In certain embodiments, the reducing gas stream can comprise (or consist essentially of, or consist of) molecular hydrogen and nitrogen.

In some embodiments, molecular hydrogen can be the major component of the reducing gas stream, while in other embodiments, molecular hydrogen can be a minor component. For example, the reducing gas stream can comprise at least about 25 mole % molecular hydrogen, at least about 35 mole % molecular hydrogen, at least about 50 mole % molecular hydrogen, at least about 65 mole % molecular hydrogen, at least about 75 mole % molecular hydrogen, or 100 mole % molecular hydrogen. Accordingly, suitable ranges for the mole % of molecular hydrogen in the reducing gas stream can include, but are not limited to, the following ranges: from about 25 to 100 mole %, from about 50 to 100 mole %, from about 25 to 100 mole %, from about 35 to 100 mole %, from about 55 to 100 mole %, from about 25 to about 75 mole %, from about 35 to about 65 mole %, or from about 70 to 100 mole %, and the like.

The reducing step can be conducted at a variety of temperatures and time periods. For instance, the reducing step can be conducted at a peak reducing temperature in a range from about 300° C. to about 600° C.; alternatively, from about 300° C. to about 550° C.; alternatively, from about 400° C. to about 600° C.; alternatively, from about 350° C. to about 575° C.; alternatively, from about 400° C. to about 550° C.; or alternatively, from about 450° C. to about 550° C. In these and other embodiments, these temperature ranges also are meant to encompass circumstances where the reducing step is conducted at a series of different temperatures (e.g., an initial reducing temperature, a peak reducing temperature), instead of at a single fixed temperature, falling within the respective ranges. For instance, the reducing step can start at an initial reducing temperature which is the same as the halogenation temperature in the halogenation step, or the fluorination temperature in the fluorination step, or the chlorination temperature in the chlorination step (e.g., in a range from about 0° C. to about 500° C., in a range from about 25° C. to about 250° C., or in a range from about 50° C. to about 280° C.). Subsequently, the temperature of the reducing step can be increased to a peak reducing temperature, for example, in a range from about 400° C. to about 600° C.

The duration of the reducing step is not limited to any particular period of time. Hence, the reducing step can be conducted, for example, in a time period ranging from as little as 1 hour to as long as 48-72 hours, or more. For example, the reducing step can be conducted in a time period that can be in a range from about 2 hours to about 48 hours, from about 3 hours to about 36 hours, from about 5 hours to about 36 hours, from about 2 hours to about 30 hours, or from about 10 hours to about 30 hours.

Alternatively, the reducing step can be conducted for a time period sufficient to result in a treated spent catalyst having an activity that is from about 50% to about 80% of the activity of the fresh catalyst, for example, from about 50% to about 75%, or from about 55% to about 75%. In this regard, the activity of the treated spent catalyst is based on returning to within about 50%-80% of fresh catalyst activity of the same production run of catalyst, tested on the same equipment and under the same method and conditions.

Reforming Processes with Aromatization Catalysts

Also encompassed herein are various processes for reforming hydrocarbons. One such reforming process can comprise (or consist essentially of, or consist of):

(a) contacting a hydrocarbon feed with an aromatization catalyst comprising a transition metal and a catalyst support under reforming conditions in a reactor system to produce an aromatic product;

(b) performing step (a) for a time period sufficient to form a spent aromatization catalyst;

(c) contacting the spent aromatization catalyst with a halogen-containing stream comprising chlorine and fluorine to produce a halogenated spent catalyst; and (d) contacting the halogenated spent catalyst with a decoking gas stream comprising oxygen.

Generally, the features of any of the reforming processes disclosed herein (e.g., the hydrocarbon feed, the aromatization catalyst, the transition metal, the catalyst support, the reforming conditions, the halogen-containing stream, the conditions under which the halogenation step is conducted, the decoking gas stream, the conditions under which the decoking step is conducted, among others) are independently described herein, and these features can be combined in any combination to further describe the disclosed processes. Moreover, other process steps can be conducted before, during, and/or after any of the steps listed in the disclosed processes, unless stated otherwise.

The halogenation step (c) and the carbon burn step (d) are discussed herein above. Any embodiments and features of the halogenation step and/or the carbon burn step (as well as other steps that can be conducted before, during and/or after the halogenation step and/or the carbon burn step) described herein can be utilized in the processes for reforming hydrocarbons and, accordingly, are encompassed herein.

Another process for reforming hydrocarbons disclosed herein can comprise (or consist essentially of, or consist of):

(A) contacting a hydrocarbon feed with an aromatization catalyst comprising a transition metal and a catalyst support under reforming conditions in a reactor system to produce an aromatic product;

(B) performing step (A) for a time period sufficient to form a spent aromatization catalyst;

(C) contacting the spent aromatization catalyst with a fluorine-containing stream comprising a fluorine-containing compound to produce a fluorinated spent catalyst;

(D) contacting the fluorinated spent catalyst with a chlorine-containing stream comprising a chlorine-containing compound to produce a fluorinated-chlorinated spent catalyst; and (E) contacting the fluorinated-chlorinated spent catalyst with a decoking gas stream comprising oxygen.

Yet another process for reforming hydrocarbons disclosed herein can comprise (or consist essentially of, or consist of):

(A) contacting a hydrocarbon feed with an aromatization catalyst comprising a transition metal and a catalyst support under reforming conditions in a reactor system to produce an aromatic product;

(B) performing step (A) for a time period sufficient to form a spent aromatization catalyst;

(C) contacting the spent aromatization catalyst with a chlorine-containing stream comprising a chlorine-containing compound to produce a chlorinated spent catalyst;

(D) contacting the chlorinated spent catalyst with a fluorine-containing stream comprising a fluorine-containing compound to produce a chlorinated-fluorinated spent catalyst; and (E) contacting the chlorinated-fluorinated spent catalyst with a decoking gas stream comprising oxygen.

Generally, the features of any of the reforming processes disclosed herein (e.g., the hydrocarbon feed, the aromatization catalyst, the transition metal, the catalyst support, the reforming conditions, the fluorine-containing stream, the conditions under which the fluorination step is conducted, the chlorine-containing stream, the conditions under which the chlorination step is conducted, the decoking gas stream, the conditions under which the decoking step is conducted, among others) are independently described herein, and these features can be combined in any combination to further describe the disclosed processes. Moreover, other process steps can be conducted before, during, and/or after any of the steps listed in the disclosed processes, unless stated otherwise.

The fluorination and chlorination steps (steps (C) and (D)) and the carbon burn step (E) are discussed herein above. Any embodiments and features of the fluorination step and/or the chlorination step and/or the carbon burn step (as well as other steps that can be conducted before, during and/or after the fluorination step and/or the chlorination step and/or the carbon burn step) described herein can be utilized in the processes for reforming hydrocarbons and, accordingly, are encompassed herein.

In these reforming processes, step (a) and step (A) can comprise contacting a hydrocarbon feed with an aromatization catalyst under reforming conditions in a reactor system to produce an aromatic product. The reactor systems for reforming and the respective reforming conditions are well known to those of skill in the art and are described, for example, in U.S. Pat. Nos. 4,456,527, 5,389,235, 5,401,386, 5,401,365, 6,207, 042, and 7,932,425, the disclosures of which are incorporated herein by reference in their entirety.

Likewise, typical hydrocarbon feeds are disclosed in these references. Often, the hydrocarbon feed can be a naptha stream or light naptha stream. In certain embodiments, the hydrocarbon feed can comprise $C_6$-$C_8$ alkanes and/or cycloalkanes (e.g., hexane, cyclohexane, etc.).

Step (b) and step (B) in the reforming processes indicate that step (a) and step (A), respectively, can be performed for a time period sufficient for the aromatization catalyst to be "spent." As discussed herein above, a "spent" catalyst is typically a catalyst that has unacceptable performance in one or more of catalyst activity, hydrocarbon feed conversion, yield to a desired product(s), selectivity to a desired product(s), or an operating parameter, such as output/production rate or reforming temperature, although not limited thereto. Once the aromatization catalyst is "spent," the rejuvenation steps (c) and (d) (or (C), (D), and (E)), amongst others, can be performed.

In an embodiment, the reforming process can be an in situ process, for example, steps (a)-(d) or (A)-(E) can be performed in the same reactor system. However, in an alternative embodiment, the catalyst treatment or rejuvenation steps (c)-(d) or (C)-(E) can be conducted external to the reactor system, such as in another vessel and/or location. For instance, the halogenation (or fluorination and chlorination) and the carbon burn steps can be conducted in a vessel that is not in the reforming reactor system.

In another embodiment, the reforming process can further comprise a step of reactivating the catalyst after step (d) or after step (E). Any catalyst reactivated by these processes is considered within the scope of this disclosure and encompassed herein. In some embodiments, the reactivated catalyst can have from about 50% to about 80% of the catalyst activity of fresh aromatization catalyst of the same production run of catalyst, tested on the same equipment, and under the same method and test conditions.

Additionally, it is contemplated that the fouling rate (FR) of the reactivated catalyst can be equal to or less than the fouling rate of the fresh aromatization catalyst. Moreover, the End of Run (EOR) temperature of the reactivated catalyst can be within +/−8° C. of the EOR temperature of the fresh aromatization catalyst, in certain embodiments.

Transition Metal Based Catalysts

Consistent with embodiments disclosed herein, and the various methods described herein above and below, the aromatization catalyst (e.g., fresh or spent) can comprise a transition metal and a catalyst support. The catalyst support typically can comprise an inorganic oxide, examples of which can include, but are not limited to, bound medium and/or large pore zeolites (aluminosilicates), amorphous inorganic oxides, as well as mixtures thereof. Large pore zeolites often can have average pore diameters in a range of from about 7 Å to about 12 Å, and non-limiting examples of large pore zeolites include L-zeolite, Y-zeolite, mordenite, omega zeolite, beta zeolite, and the like. Medium pore zeolites often can have average pore diameters in a range of from about 5 Å to about 7 Å. Amorphous inorganic oxides can include, but are not limited to, aluminum oxide, silicon oxide, titania, and combinations thereof.

The term "zeolite" generally refers to a particular group of hydrated, crystalline metal aluminosilicates. These zeolites exhibit a network of $SiO_4$ and $AlO_4$ tetrahedra in which aluminum and silicon atoms are crosslinked in a three-dimensional framework by sharing oxygen atoms. In the framework, the ratio of oxygen atoms to the total of aluminum and silicon atoms can be equal to 2. The framework exhibits a negative electrovalence that typically can be balanced by the inclusion of cations within the crystal, such as metals, alkali metals, alkaline earth metals, and/or hydrogen.

In some embodiments, the catalyst support can comprise an L-type zeolite. L-type zeolite supports are a sub-group of zeolitic supports, which can contain mole ratios of oxides in accordance with the formula: $M_{2/n}OAl_2O_3xSiO_2yH_2O$. In this formula, "M" designates an exchangeable cation (one or more) such as barium, calcium, cerium, lithium, magnesium, potassium, sodium, strontium, and/or zinc, as well as non-metallic cations like hydronium and ammonium ions, which may be replaced by other exchangeable cations without causing a substantial alteration of the basic crystal structure of the L-type zeolite. The "n" in the formula represents the valence of "M"; "x" is 2 or greater; and "y" is the number of water molecules contained in the channels or interconnected voids of the zeolite.

In one embodiment, the catalyst support can comprise a bound potassium L-type zeolite, also referred to as a KL-zeolite, while in another embodiment, the catalyst support can comprise a barium ion-exchanged L-zeolite. As used herein, the term "KL-zeolite" refers to L-type zeolites in which the principal cation M incorporated in the zeolite is potassium. A KL-zeolite can be cation-exchanged (e.g., with barium) or impregnated with a transition metal and one or more halides to produce a transition metal impregnated, halided zeolite or a KL supported transition metal-halide zeolite catalyst.

In the aromatization catalyst (e.g., fresh or spent), the zeolite can be bound with a support matrix (or binder), non-limiting examples of which can include silica, alumina, magnesia, boria, titania, zirconia, various clays, and the like, including mixed oxides thereof, as well as mixtures thereof. For example, the spent catalyst can comprise a support matrix comprising alumina, silica, a mixed oxide thereof, or a mixture thereof. The zeolite can be bound with the support matrix using any method known in the art.

The aromatization catalyst can comprise a transition metal, and non-limiting examples of suitable transition metals can include iron, cobalt, nickel, ruthenium, rhodium, palladium, osmium, iridium, platinum, gold, silver, copper, and the like, or a combination of two or more transition metals. In one embodiment, the transition metal can comprise a Group VIII transition metal (one or more), while in another embodiment, the transition metal can comprise platinum (Pt).

In one embodiment, the spent catalyst can comprise from about 0.1 wt. % to about 10 wt. % transition metal. In another embodiment, the spent catalyst can comprise from about 0.3 wt. % to about 5 wt. % transition metal. In yet another embodiment, the spent catalyst can comprise from about 0.3 wt. % to about 3 wt. % transition metal, or from about 0.5 wt. % to about 2 wt. % transition metal. These weight percentages are based on the weight of the spent catalyst excluding carbon. As one of skill in the art would recognize, the spent catalyst can contain varying levels of carbon build-up, often in the 2 wt. % to 10 wt. % range. Accordingly, the weight percentages of the transition metal are meant to be based on the weight of the spent catalyst minus any weight attributable to carbon.

In circumstances where the transition metal comprises platinum, the spent catalyst can comprise from about 0.1 wt. % to about 10 wt. % platinum; alternatively, from about 0.3 wt. % to about 5 wt. % platinum; alternatively, from about 0.3 wt. % to about 3 wt. % platinum; or alternatively, from about 0.5 wt. % to about 2 wt. % platinum. In a particular embodiment contemplated herein, the spent catalyst can comprise platinum on a KL-zeolite.

While not being limited thereof, the spent catalyst can comprise from about 5 wt. % to about 35 wt. % support matrix. For example, the spent catalyst can comprise from about 5 wt. % to about 30 wt. %, or from about 10 wt. % to about 30 wt. % support matrix. Similar to above, these weight percentages are based on the weight of the spent catalyst excluding any weight contribution due to carbon.

In an embodiment, the aromatization catalyst can further comprise a halogen, such as chlorine, fluorine, bromine, iodine, or a combination of two or more halogens. For example, the spent catalyst can comprise chlorine, or fluorine, or both chlorine and fluorine. Chlorine can be present in the spent catalyst in an amount of from about 0.025 wt. % to about 5 wt. %, from about 0.025 wt. % to about 3 wt. %, or from about 0.05 wt. % to about 2 wt. %. Likewise, the spent catalyst can comprise from about 0.025 wt. % to about 5 wt. % fluorine, from about 0.025 wt. % to about 3 wt. % fluorine, or from about 0.05 wt. % to about 2 wt. % fluorine. These weight percentages are based on the weight of the spent catalyst, and exclude any weight contribution due to carbon. In certain embodiments, the spent catalyst comprises chlorine and fluorine, and typically, the molar ratio of chlorine:fluorine can be in the range of from about 0.5:1 to about 4:1. Other suitable molar ratios of Cl:F can include the following non-limiting ranges: from about 1:1 to about 4:1, from about 0.5:1 to about 3:1, from about 1:1 to about 3:1, from about 0.5:1 to about 2:1, or from about 1:1 to about 2.5:1.

Examples of representative and non-limiting catalysts that are encompassed herein include those disclosed in U.S. Pat. Nos. 5,196,631, 6,190,539, 6,406,614, 6,518,470, 6,812,180, and 7,153,801, the disclosures of which are incorporated herein by reference in their entirety.

EXAMPLES

The invention is further illustrated by the following examples, which are not to be construed in any way as imposing limitations to the scope of this invention. Various other aspects, embodiments, modifications, and equivalents thereof which, after reading the description herein, can suggest themselves to one of ordinary skill in the art without departing from the spirit of the present invention or the scope of the appended claims.

Treated or rejuvenated catalysts in some of the examples that follow were tested for their respective fouling rates (abbreviated FR, units of m° F./hr), which correlate to their activities by the formula, y=FR*t+SOR, where y is temperature, FR is the fouling rate, t is time, and SOR is the initial Start of Run temperature. The FR of a treated or rejuvenated catalyst sample was determined by plotting the temperature required to maintain a total yield of benzene and toluene at 60 wt. % over time at standard test conditions, as described later herein. The FR's were then determined from the calculated slopes fit to the resulting data. The total Time on Stream (abbreviated TOS, units of hr) and the End of Run temperature (abbreviated EOR) also were determined.

In each of the examples, the following standard testing procedures were utilized. The catalysts were ground and sieved to about 20-40 mesh, and 1 g of the sieved catalyst was placed in a ¼-inch OD stainless steel reactor vessel in a temperature controlled furnace. After reducing the catalyst under flowing molecular hydrogen, a feed stream of aliphatic hydrocarbons and molecular hydrogen was introduced to the reactor vessel at a feed rate of 22 mL/min, a pressure of 50 psig, a $H_2$:hydrocarbon molar ratio of 3:1, and a liquid hourly space velocity (LHSV) of 9 hr$^{-1}$ to obtain catalyst performance data over time. The aliphatic hydrocarbon feed contained from 22 to 26 wt. % n-hexane, 4 to 8 wt. % n-heptane, 33 to 37 wt. % $C_6$ iso-paraffins, 17 to 21 wt. % $C_7$ iso-paraffins, 6 to 10 wt. % $C_8$ iso-paraffins, with the balance attributable to $C_6$ and $C_7$ olefins, naphthenes, and aromatics. The reactor effluent composition was analyzed by gas chromatography to determine the amount of benzene and toluene.

Examples 1-47

In Examples 1-47, experiments were conducted to demonstrate the effectiveness of various processes and steps in treating and rejuvenating a spent aromatization catalyst, with the performance of a fresh aromatization catalyst used as a target baseline. The fresh aromatization catalyst was a Pt/KL-zeolite containing approximately 1 wt. % platinum, and 0.828 wt. % Cl and 0.837 wt. % F (determined via XRF), with a surface area of approximately 177.5 $m^2/g$, a pore volume of 0.19 cc/g, and a micropore volume of 0.0615 cc/g. The source of the spent catalyst was the fresh catalyst, but after it had been deactivated after long-term use in an aromatization process. Prior to usage in these examples, the spent aromatization catalyst was subjected to a mild partial decoking treatment to remove unreacted hydrocarbons and light carbonaceous deposits from the catalyst.

The general treating or rejuvenating procedure was conducted as follows. Approximately 62 g of the spent catalyst was charged to a glass fixed-bed reactor, then contacted with a halogen-containing gas stream containing nitrogen (1850 mL/min), chlorine gas (2 volume % in nitrogen, 50 mL/min), and fluorine gas (1 volume % in nitrogen, 100 mL/min). The spent catalyst was contacted for 6 hr at 200° C. with the halogen-containing gas stream. The halogenated spent catalyst was then contacted with a decoking gas stream containing a mixture of air (100 mL/min) and nitrogen (1900 mL/min). The reactor temperature was ramped slowly from 200° C. to 500° C. over 8 hr and then held at 500° C. for 24 hr. Molecular hydrogen (1330 mL/min) was then contacted with the de-coked catalyst at 500° C. for 20 hr. This general procedure was followed for Examples 1-47, except for the process changes to this general procedure noted in the discussion of Examples 1-47 below. Table I summarizes the rejuvenation results for Examples 1-47.

In Examples 1-9, Example 1 was the fresh catalyst baseline. For Example 2, the carbon burn step was performed on the spent catalyst at a peak temperature of 550° C., followed by halogenation with $Cl_2/F_2$ (volume ratio of 2:1) at 300° C. For Example 3, the sequence of steps was reversed: the spent catalyst was halogenated with $Cl_2/F_2$ (volume ratio of 2:1) at 300° C., followed by the carbon burn step at a peak temperature of 550° C. Unexpectedly, the order of the steps resulted in significantly different catalyst performance. The spent catalyst which was halogenated first (Example 3) had a much lower SOR temperature, as compared to the spent catalyst which was de-coked first (928° F. versus 994° F.), demonstrating the unexpected benefit of performing the halogenation step prior to the carbon burn step.

For Examples 4-5, halogenation of the spent catalyst with $Cl_2/F_2$ was conducted at 300° C. In Example 4, the halogenation gas stream contained 1000 ppmv of $Cl_2$, 500 ppmv $F_2$, 1 volume % $O_2$, and the balance $N_2$, while the halogenation gas stream of Example 5 contained 500 ppmv of $Cl_2$, 500 ppmv $F_2$, 1 volume % $O_2$, and the balance $N_2$. Hence, the volume ratio of Cl:F was 2:1 in Example 4 and 1:1 in Example 5. Surprisingly, the reduction in the Cl:F ratio resulted in only minor decreases in catalyst performance: SOR from 914° F. to 916° F., and FR from 28 to 33 m° F./hr.

For Examples 6-9, halogenation with $Cl_2/F_2$ (volume ratio of 2:1) was first conducted at 300° C., followed by the carbon burn step at a peak temperature of 550° C., 500° C., 475° C., or 450° C., respectively. Unexpectedly, the results demonstrated that the peak temperature of the carbon burn can be reduced to 450° C. (Example 9) from 550° C. (Example 6) with only a minor loss of catalyst activity: SOR temperature increased from 928° F. to 952° F., and fouling rate FR increased from 14 to 30 m° F./hr.

In Examples 10-14, Example 10 was the fresh catalyst baseline. For Examples 11-14, the spent catalyst was halogenated with $Cl_2/F_2$ (volume ratio of 2:1) at a temperature of 300° C., 200° C., 100° C., or room temperature, respectively. The results demonstrated that halogenation temperatures over 100° C. (e.g., 200-300° C., Examples 11-12) improved the catalyst performance. At temperatures of 100° C. and below, inferior catalysts with higher SOR temperatures and higher fouling rates were produced.

In Examples 15-18, Example 15 was the fresh catalyst baseline. The spent catalyst of Example 16 was pre-dried in a mixture of air (100 mL/min) and nitrogen (1900 mL/min) at 260° C., the spent catalyst of Example 17 was pre-dried in $N_2$, and the spent catalyst in Example 18 was not pre-dried. Subsequent halogenation with $Cl_2/F_2$ (volume ratio of 1:1) was conducted at 260° C. for these examples. Purging of Examples 16-17 was conducted in a mixture of air and nitrogen at 260° C. De-coking of Examples 16-18 was conducted at 500° C. Surprisingly, pre-drying in an inert gas prior to halogenation and subsequent carbon burn (Example 17; SOR 914° F.) produced a far superior catalyst compared to that formed by pre-drying in an air/nitrogen mixture (Example 16; SOR 927° F.).

In Examples 19-32, Example 19 was the fresh catalyst baseline. Each of the spent catalysts of Examples 20-23 was pre-dried in $N_2$ at 200° C. Subsequent halogenation with $Cl_2/F_2$ (volume ratio of 1:1) was conducted at 200° C. in a mixture of air and nitrogen for Example 20, at 200° C. in nitrogen for Example 21, at 260° C. in a mixture of air and nitrogen for Example 22, and at 260° C. in nitrogen for Example 23. Decoking of all examples was conducted in a mixture of air and nitrogen at 500° C. Unexpectedly, the composition of the gas stream during halogenation affected the catalyst performance. Rejuvenated catalyst produced using an inert gas (e.g., Example 21; SOR 916° F.) during the halogenation step performed better than the catalyst produced when an air/nitrogen mixture was used (e.g., Example 20 SOR 930° F.).

Each of the spent catalysts of Examples 24-25 was pre-dried in $N_2$ at 200° C., halogenated in a mixture of air and nitrogen with $Cl_2/F_2$ (volume ratio of 1:1) at 200° C., and de-coked at 500° C. Prior to the pre-drying step, the spent catalyst of Example 25 underwent a re-coking pretreatment at 500° C. with molecular hydrogen and an aromatization feed containing $C_6$-$C_8$ alkanes and/or cycloalkanes and less than 5 wt. % aromatics, while Example 24 was not pretreated. More specifically, the aromatization feed used contained from 22 to 26 wt. % n-hexane, 4 to 8 wt. % n-heptane, 33 to 37 wt. % $C_6$ iso-paraffins, 17 to 21 wt. % $C_7$ iso-paraffins, 6 to 10 wt. % $C_8$ iso-paraffins, with the balance attributable to $C_6$ and $C_7$ olefins, naphthenes, and aromatics. Surprisingly, the re-coking pretreatment prior to halogenation significantly improved catalyst activity. Rejuvenated catalyst using the re-coking pretreatment (Example 25; SOR 917° F.) had improved performance over the untreated catalyst (Example 24; SOR 930° F.).

Each of the spent catalysts of Examples 26-29 was halogenated in nitrogen with $Cl_2/F_2$ (volume ratio of 1:1) at 200°

C., and de-coked at 500° C. A subsequent reduction step was conducted with 10 mole % $H_2$ in nitrogen at 500° C. for Example 26, with 100% $H_2$ at 500° C. for Example 27, with 20 mole % $H_2$ in nitrogen at 500° C. for Example 28, and with 100% $H_2$ at 500° C. for Example 29 (duplicate of Example 27). Unexpectedly, the amount of molecular hydrogen present in the reducing step affected the catalyst performance. Rejuvenated catalysts produced with high mole % molecular hydrogen (Examples 27 and 29) during the reducing step performed better than the catalysts produced when low mole % molecular hydrogen was used.

Each of the spent catalysts of Examples 30-32 was halogenated in a nitrogen stream containing $Cl_2/F_2$, de-coked in a mixture of air and nitrogen at 500° C., and reduced in 100% $H_2$ at 500° C. In Example 30, the halogenation gas stream contained 500 ppmv of $Cl_2$ and 500 ppmv $F_2$ and the halogenation time was 6 hr; in Example 31, the halogenation gas stream contained 1,100 ppmv of $Cl_2$ and 1,100 ppmv $F_2$ and the halogenation time was 3 hr; and in Example 32, the halogenation gas stream contained 2,200 ppmv of $Cl_2$ and 2,200 ppmv $F_2$ and the halogenation time was 1.5 hr. The results demonstrated that the time for the halogenation step can be reduced with an increase in the halogen concentration in the nitrogen stream (e.g., 1,100 ppmv each of $Cl_2$ and $F_2$ for 3 hr in Example 31).

In Examples 33-37, Example 33 was the fresh catalyst baseline. Example 34 was not subjected to any hydrocarbon treatment, while Example 35 was hydrocarbon treated before halogenation, Example 36 was hydrocarbon treated during halogenation, and Example 37 was hydrocarbon treated after halogenation but before the carbon burn step. Halogenation was performed under inert conditions with $Cl_2/F_2$ (volume ratio of 1:1), and the carbon burn was conducted in the mixture of air and nitrogen. Similar to Example 25, the hydrocarbon treatment stream was the aromatization feed (containing from 22 to 26 wt. % n-hexane, 4 to 8 wt. % n-heptane, 33 to 37 wt. % $C_6$ iso-paraffins, 17 to 21 wt. % $C_7$ iso-paraffins, 6 to 10 wt. % $C_8$ iso-paraffins, with the balance attributable to $C_6$ and $C_7$ olefins, naphthenes, and aromatics), but with no molecular hydrogen. As with Example 25, the hydrocarbon treatment prior to halogenation of Example 35 was beneficial. Surprisingly, however, the hydrocarbon treatment after halogenation, but before the carbon burn step, of Example 37 was even more beneficial in improving rejuvenated catalyst performance.

In Examples 38-47, Example 38 was the fresh catalyst baseline. For Examples 39-41, the spent catalyst was halogenated with $Cl_2/F_2$ (volume ratio of 1:1) in nitrogen at a temperature of 200° C., 260° C., or 370° C., respectively. Unexpectedly, the results demonstrated that the lower halogenation temperatures of 200-260° C. provided superior catalyst performed as compared to the higher halogenation temperature of 370° C.

For Examples 42-45, halogenation of the spent catalyst with $Cl_2/F_2$ was conducted at 260° C. The volume ratio of Cl:F was 2:1 in Example 42, 1:1 in Example 43, 0.67:1 in Example 44, and 0.5:1 in Example 45. Under these conditions, the rejuvenated catalyst with the best overall catalyst performance was obtained at a Cl:F ratio of 1:1.

Each of the spent catalysts of Examples 46-47 was halogenated with $Cl_2/F_2$ (volume ratio of 1:1) at 200° C., and de-coked in the mixture of air and nitrogen at 500° C. The carbon burn time for Example 46 was 16 hr, while the carbon burn time for Example 47 was 1 hr. The gas stream after contacting the spent catalyst was monitored for carbon dioxide levels to determine when sufficient de-coking had occurred. In these examples, 1 hr at 500° C. was sufficient for the carbon burn step.

TABLE I

Examples 1-47.

| Example | Catalyst | SOR T60 (° F.) | TOS. (hr) | EOR T60 (° F.) | FR (m ° F./hr) |
|---|---|---|---|---|---|
| 1 | Fresh | 911 | 140 | 919 | 56.4 |
| 2 | Spent | 994 | — | — | — |
| 3 | Spent | 928 | 140 | 929 | 14.0 |
| 4 | Spent | 914 | 163 | 918 | 28.2 |
| 5 | Spent | 916 | 164 | 922 | 33.2 |
| 6 | Spent | 928 | 140 | 929 | 14.0 |
| 7 | Spent | 914 | 163 | 918 | 28.2 |
| 8 | Spent | 911 | 164 | 917 | 37.4 |
| 9 | Spent | 952 | 163 | 956 | 30.3 |
| 10 | Fresh | 906 | 138 | 910 | 28.0 |
| 11 | Spent | 914 | 163 | 918 | 28.2 |
| 12 | Spent | 912 | 163 | 914 | 18.4 |
| 13 | Spent | 963 | 68 | 966 | 44.0 |
| 14 | Spent | 991 | 20 | 1000 | — |
| 15 | Fresh | 911 | 140 | 919 | 56.4 |
| 16 | Spent | 927 | 140 | 936 | 67.8 |
| 17 | Spent | 914 | 163 | 921 | 43.6 |
| 18 | Spent | 913 | 116 | 924 | 93.7 |
| 19 | Fresh | 902 | 168 | 902 | 1.9 |
| 20 | Spent | 930 | 43 | 932 | 44.4 |
| 21 | Spent | 916 | 120 | 915 | — |
| 22 | Spent | 913 | 96 | 914 | 13.1 |
| 23 | Spent | 910 | 145 | 912 | 14.7 |
| 24 | Spent | 930 | 43 | 932 | 44.4 |
| 25 | Spent | 917 | 144 | 919 | 18.5 |
| 26 | Spent | 908 | 120 | 912 | 40.9 |
| 27 | Spent | 906 | 144 | 907 | 17.0 |
| 28 | Spent | 913 | 144 | 920 | 55.4 |
| 29 | Spent | 905 | 144 | 909 | 31.2 |
| 30 | Spent | 906 | 144 | 907 | 17.0 |
| 31 | Spent | 905 | 144 | 908 | 16.7 |
| 32 | Spent | 909 | 144 | 912 | 19.0 |
| 33 | Fresh | 898 | 144 | 906 | 54.3 |
| 34 | Spent | 912 | 96 | 917 | 56.0 |
| 35 | Spent | 909 | 144 | 915 | 44.2 |
| 36 | Spent | 988 | 24 | 979 | — |
| 37 | Spent | 904 | 120 | 904 | 12.8 |
| 38 | Fresh | 902 | 144 | 907 | 55.5 |
| 39 | Spent | 914 | 144 | 917 | 28.9 |
| 40 | Spent | 908 | 144 | 914 | 38.3 |
| 41 | Spent | 928 | 120 | 933 | 50.2 |
| 42 | Spent | 927 | 72 | 930 | 46.2 |
| 43 | Spent | 908 | 144 | 914 | 38.3 |
| 44 | Spent | 919 | 143 | 922 | 30.7 |
| 45 | Spent | 917 | 144 | 925 | 68.5 |
| 46 | Spent | 917 | 138 | 922 | 45.6 |
| 47 | Spent | 914 | 144 | 917 | 28.9 |

Examples 48-49

The fresh aromatization catalyst (Example 48) was a Pt/KL-zeolite containing approximately 1 wt. % platinum, and 0.828 wt. % Cl and 0.837 wt. % F (determined via XRF), with a surface area of approximately 177.5 $m^2/g$, a pore volume of 0.19 cc/g, and a micropore volume of 0.0615 cc/g. The source of the spent catalyst was the fresh catalyst, but after it has been deactivated after long-term use in an aromatization process. Prior to usage in these examples, the spent aromatization catalyst was subjected to a mild partial decoking treatment at 200° C. to remove unreacted hydrocarbons and light carbonaceous deposits from the catalyst.

The rejuvenation process was conducted as follows. Approximately 62 g of the spent catalyst was charged to a glass fixed-bed reactor, and contacted with a pre-drying gas stream containing nitrogen (2000 mL/min) at 200° C. for 20 hr. The gas stream was changed to a halogen-containing gas stream containing nitrogen (1750 mL/min), chlorine gas (2 volume % in nitrogen, 50 mL/min), and fluorine gas (1 volume % in nitrogen, 200 mL/min), and the spent catalyst was contacted for 3 hr at 200° C. with the halogen-containing gas stream. The halogenated spent catalyst was then contacted with a purging gas stream containing nitrogen (2000 mL/min) at 200° C. for 20 hr. Next, a decoking gas stream was charged to the reactor and contacted with the halogenated spent catalyst. The decoking gas stream contained air (100 mL/min) and nitrogen (1900 mL/min). The reactor temperature was ramped slowly from 200° C. to 500° C. over 6 hr and then held at 500° C. for 20 hr. The reactor and the de-coked catalyst were cooled down with a mixture of air (100 mL/min) and nitrogen (1900 mL/min). This rejuvenated catalyst is Example 49.

The catalyst performance of the rejuvenated catalyst of Example 49 was compared to that of the fresh catalyst of Example 48. An aromatization feedstock was used for the catalyst comparison. The results indicated that the catalyst activity of the rejuvenated catalyst of Example 49 was slightly lower than the fresh catalyst of Example 48, while the selectivity using the rejuvenated catalyst was equal to or superior to that of the fresh catalyst.

Examples 50-55

The fresh aromatization catalyst (Example 50) was a Pt/KL-zeolite containing approximately 1 wt. % platinum, and 0.828 wt. % Cl and 0.837 wt. % F (determined via XRF), with a surface area of approximately 177.5 m²/g, a pore volume of 0.19 cc/g, and a micropore volume of 0.0615 cc/g. The source of the spent catalyst was the fresh catalyst, but after it has been deactivated after long-term use in an aromatization process. This spent catalyst had less carbon/coke deposition than that of the spent catalyst in Examples 48-49. Prior to usage in these examples, the spent aromatization catalyst was subjected to a mild partial decoking treatment at 200° C. to remove unreacted hydrocarbons and light carbonaceous deposits from the catalyst. The spent catalyst (Example 51) contained approximately 1 wt. % platinum, 0.19 wt. % Cl, and 0.05 wt. % F (determined via XRF).

The rejuvenation process was conducted as follows. Approximately 61 g of the spent catalyst was charged to a glass fixed-bed reactor, and contacted with a pre-drying gas stream containing nitrogen (2000 mL/min) at 200° C. for 20 hr. The gas stream was changed to a halogen-containing gas stream containing nitrogen (1750 mL/min), chlorine gas (2 volume % in nitrogen, 50 mL/min), and fluorine gas (1 volume % in nitrogen, 200 mL/min), and the spent catalyst was contacted for 3 hr at 200° C. with the halogen-containing gas stream. The halogenated spent catalyst was then contacted with a purging gas stream containing nitrogen (2000 mL/min) at 200° C. for 20 hr. Next, a decoking gas stream was charged to the reactor and contacted with the halogenated spent catalyst. The decoking gas stream contained air (100 mL/min) and nitrogen (1900 mL/min). The reactor temperature was ramped slowly from 200° C. to a peak decoking temperature in the 400-500° C. range over 6 hr and then held at the peak temperature for up to 44 hr (Examples 52-55). The reactor and the de-coked catalyst were cooled down with a mixture of air (100 mL/min) and nitrogen (1900 mL/min). Table II summarizes various decoking conditions and the resultant rejuvenated catalyst properties.

TABLE II

Examples 50-55.

| Example | Catalyst | Peak Decoking (° C.) | Decoking Time (hr) | Wt. % Pt | Wt. % Cl | Wt. % F | Surface Area (m2/g) | Pore Volume (cc/g) | Mirco-Pore Volume (cc/g) |
|---|---|---|---|---|---|---|---|---|---|
| 50 | Fresh | — | — | 1 | 0.828 | 0.837 | 177 | 0.191 | 0.0615 |
| 51 | Spent | — | — | 0.999 | 0.188 | 0.046 | — | — | — |
| 52 | — | 500 | 16 | 0.991 | 0.621 | 0.632 | 87 | 0.131 | 0.0285 |
| 53 | — | 435 | 16 | 0.993 | 0.644 | 0.733 | 99 | 0.147 | 0.0260 |
| 54 | — | 400 | 20 | 0.976 | 0.682 | 0.808 | 94 | 0.149 | 0.0290 |
| 55 | — | 400 | 44 | 0.967 | 0.640 | 0.695 | 98 | 0.150 | 0.0265 |

Examples 56-60

In Examples 56-60, the spent aromatization catalyst and general treating or rejuvenating procedure were the same as provided above for Examples 1-47, except for the process changes as follows. For Examples 56-58, the halogenation gas stream contained 500 ppmv of $Cl_2$, 1000 ppmv $F_2$, and the balance $N_2$ (volume ratio of Cl:F equal to 1:2), and the halogenation step was conducted for 3 hr at a temperature of 200° C., 100° C., and 25° C. (ambient), respectively. For Example 59, the spent catalyst was first contacted with a chlorination gas stream containing 500 ppmv of $Cl_2$ (balance $N_2$) for 3 hr at 200° C., then contacted with a fluorination gas stream containing 1000 ppmv of $F_2$ (balance $N_2$) for 3 hr at 25° C. (ambient). For Example 60, the spent catalyst was first contacted with a fluorination gas stream containing 1000 ppmv of $F_2$ (balance $N_2$) for 3 hr at 25° C. (ambient), then contacted with a chlorination gas stream containing 500 ppmv of $Cl_2$ (balance $N_2$) for 3 hr at 200° C.

Table III summarizes the initial Start of Run temperature (SOR) to maintain the total yield of benzene and toluene at 60 wt. % over time at the standard test conditions described above, as well as the SOR temperature to maintain the total yield of benzene and toluene at 75 wt. % over time at the same standard test conditions. Unexpectedly, the sequential addition of fluorine followed by chlorine at the respective temperatures resulted in a rejuvenated catalyst with superior performance (Example 60; SOR(60) equal to 907° F., and SOR (75) equal to 948° F.).

TABLE III

Examples 56-60.

| Example | Catalyst | SOR T60 (° F.) | SOR T75 (° F.) |
|---|---|---|---|
| 56 | Spent | 921 | 962 |
| 57 | Spent | 930 | — |
| 58 | Spent | 950 | 999 |

TABLE III-continued

Examples 56-60.

| Example | Catalyst | SOR T60 (° F.) | SOR T75 (° F.) |
|---|---|---|---|
| 59 | Spent | 947 | 991 |
| 60 | Spent | 907 | 948 |

Examples 61-63

For Examples 62-63, Example 61 was the fresh catalyst baseline. In Examples 62-63, the spent aromatization catalyst and general treating or rejuvenating procedure were the same as provided above for Examples 1-47, except for the process changes as follows. For Example 62, 60 g of the spent catalyst was first contacted with a fluorination gas stream containing 500 ppmv of $F_2$ (balance $N_2$) for 3 hr at 25° C. (ambient), then contacted with a chlorination gas stream containing 500 ppmv of $Cl_2$ (balance $N_2$) for 3 hr at 200° C. For Example 63, 60 g of the spent catalyst was first contacted with a fluorination gas stream containing 250 ppmv of $F_2$ (balance $N_2$) for 6 hr at 25° C. (ambient), then contacted with a chlorination gas stream containing 250 ppmv of $Cl_2$ (balance $N_2$) for 6 hr at 200° C.

Table IV summarizes the initial Start of Run temperature (SOR) to maintain the total yield of benzene and toluene at 60 wt. % over time at the standard test conditions described above, as well as the SOR temperature to maintain the total yield of benzene and toluene at 75 wt. % over time at the same standard test conditions. The respective total time on stream (TOS) and yield of $C_4$ by-products at both 60 wt. % and at 75 wt. % also are listed in Table IV. Notably, based on the SOR temperatures, the catalysts of both Example 62 and Example 63 performed similar to that of the fresh catalyst of Example 61. The amount of $C_4$ by-products, surprisingly, was reduced by using lower fluorine and chlorine concentrations during the catalyst rejuvenation (Example 63).

TABLE IV

Examples 61-63.

| Example | Catalyst | SOR T60 (° F.) | TOS$_{60}$ (hr) | $C_4$ @ 60 (wt. %) | SOR T75 (° F.) | TOS$_{75}$ (hr) | $C_4$ @ 75 (wt. %) |
|---|---|---|---|---|---|---|---|
| 61 | Fresh | 902 | 55 | 3.1 | 954 | 336 | 4.3 |
| 62 | Spent | 899 | 55 | 3.0 | 953 | 336 | 5.2 |
| 63 | Spent | 906 | 48 | 2.6 | 954 | 336 | 3.9 |

The invention has been described above with reference to numerous embodiments and specific examples. Many variations will suggest themselves to those skilled in the art in light of the above detailed description. All such obvious variations are within the full intended scope of the appended claims. Other embodiments of the invention can include, but are not limited to, the following:

Embodiment 1

A reforming method comprising:
(A) contacting a hydrocarbon feed with an aromatization catalyst comprising a transition metal and a catalyst support under reforming conditions in a reactor system to produce an aromatic product;
(B) performing step (A) for a time period sufficient to form a spent aromatization catalyst;
(C) contacting the spent aromatization catalyst with a fluorine-containing stream comprising a fluorine-containing compound to produce a fluorinated spent catalyst;
(D) contacting the fluorinated spent catalyst with a chlorine-containing stream comprising a chlorine-containing compound to produce a fluorinated-chlorinated spent catalyst; and
(E) contacting the fluorinated-chlorinated spent catalyst with a decoking gas stream comprising oxygen.

Embodiment 2

A reforming method comprising:
(A) contacting a hydrocarbon feed with an aromatization catalyst comprising a transition metal and a catalyst support under reforming conditions in a reactor system to produce an aromatic product;
(B) performing step (A) for a time period sufficient to form a spent aromatization catalyst;
(C) contacting the spent aromatization catalyst with a chlorine-containing stream comprising a chlorine-containing compound to produce a chlorinated spent catalyst;
(D) contacting the chlorinated spent catalyst with a fluorine-containing stream comprising a fluorine-containing compound to produce a chlorinated-fluorinated spent catalyst; and
(E) contacting the chlorinated-fluorinated spent catalyst with a decoking gas stream comprising oxygen.

Embodiment 3

The method defined in embodiment 1 or 2, wherein the reforming method is an in situ process, for example, steps (A)-(E) are performed in the same reactor system.

Embodiment 4

The method defined in embodiment 1 or 2, wherein steps (C)-(E) are performed externally to the reactor system of steps (A)-(B), for example, steps (C)-(E) are performed in a vessel that is not in the reforming reactor system.

Embodiment 5

The method defined in any of embodiments 1-4, further comprising a step of reactivating the catalyst after step (E).

Embodiment 6

A method of treating (or regenerating) a spent catalyst comprising a transition metal and a catalyst support, the method comprising:
(1) contacting the spent catalyst with a fluorine-containing stream comprising a fluorine-containing compound to produce a fluorinated spent catalyst;
(2) contacting the fluorinated spent catalyst with a chlorine-containing stream comprising a chlorine-containing compound to produce a fluorinated-chlorinated spent catalyst; and
(3) contacting the fluorinated-chlorinated spent catalyst with a decoking gas stream comprising oxygen.

Embodiment 7

A method of treating (or regenerating) a spent catalyst comprising a transition metal and a catalyst support, the method comprising:

(1) contacting the spent catalyst with a chlorine-containing stream comprising a chlorine-containing compound to produce a chlorinated spent catalyst;

(2) contacting the chlorinated spent catalyst with a fluorine-containing stream comprising a fluorine-containing compound to produce a chlorinated-fluorinated spent catalyst; and (3) contacting the chlorinated-fluorinated spent catalyst with a decoking gas stream comprising oxygen.

Embodiment 8

The method defined in any of embodiments 1-7, wherein the fluorine-containing stream comprises (or consists essentially of, or consists of) the fluorine-containing compound and any inert gas disclosed herein, for example, nitrogen.

Embodiment 9

The method defined in any of embodiments 1-8, wherein the fluorine-containing stream comprises (or consists essentially of, or consists of) fluorine gas ($F_2$) and nitrogen.

Embodiment 10

The method defined in any of embodiments 1-9, wherein the fluorine-containing stream comprises a concentration of fluorine (F) less than any maximum amount or in any range disclosed herein, for example, less than about 25,000 ppmv, in a range from about 50 to about 2,500 ppmv, or in a range from about 250 to about 2,000 ppmv.

Embodiment 11

The method defined in any of embodiments 1-10, wherein the fluorine-containing stream is substantially free of oxygen-containing compounds and/or chlorine-containing compounds, for example, less than 100 ppmw.

Embodiment 12

The method defined in any of embodiments 1-11, wherein the fluorination step is conducted at a fluorination temperature in any fluorination temperature range disclosed herein, for example, from about 0° C. to about 500° C., from about 25° C. to about 250° C., or from about 50° C. to about 280° C.

Embodiment 13

The method defined in any of embodiments 1-12, wherein the fluorination step is conducted for a time period in any range of fluorination time periods disclosed herein, for example, from about 1 to about 48 hours, from about 1 to about 12 hours, or from about 2 to about 8 hours.

Embodiment 14

The method defined in any of embodiments 1-13, wherein the chlorine-containing stream comprises (or consists essentially of, or consists of) the chlorine-containing compound and any inert gas disclosed herein, for example, nitrogen.

Embodiment 15

The method defined in any of embodiments 1-14, wherein the chlorine-containing stream comprises (or consists essentially of, or consists of) chlorine gas ($Cl_2$) and nitrogen.

Embodiment 16

The method defined in any of embodiments 1-15, wherein the chlorine-containing stream comprises a concentration of chlorine (CO less than any maximum amount or in any range disclosed herein, for example, less than about 25,000 ppmv, in a range from about 50 to about 2,500 ppmv, or in a range from about 250 to about 2,000 ppmv.

Embodiment 17

The method defined in any of embodiments 1-16, wherein the chlorine-containing stream is substantially free of oxygen-containing compounds and/or fluorine-containing compounds, for example, less than 100 ppmw.

Embodiment 18

The method defined in any of embodiments 1-17, wherein the chlorination step is conducted at a chlorination temperature in any chlorination temperature range disclosed herein, for example, from about 0° C. to about 500° C., from about 25° C. to about 250° C., or from about 50° C. to about 280° C.

Embodiment 19

The method defined in any of embodiments 1-18, wherein the chlorination step is conducted for a time period in any range of chlorination time periods disclosed herein, for example, from about 1 to about 48 hours, from about 1 to about 12 hours, or from about 2 to about 8 hours.

Embodiment 20

The method defined in any of the preceding embodiments, wherein the method further comprises a halogen purge step between step (C) and (D) or between step (1) and (2), the halogen purge step comprising contacting the fluorinated spent catalyst or chlorinated spent catalyst with a halogen purge stream comprising (or consisting essentially of, or consisting of) any inert gas disclosed herein, for example, nitrogen.

Embodiment 21

The method defined in embodiment 20, wherein the halogen purge stream is substantially free of oxygen-containing compounds, for example, less than 100 ppmw.

Embodiment 22

The method defined in any of embodiments 20-21, wherein the halogen purge stream is substantially free of halogen-containing compounds (substantially halogen-free), for example, less than 100 ppmw.

Embodiment 23

The method defined in any of embodiments 20-22, wherein the halogen purge step is conducted at a halogen purge temperature in any halogen purge temperature range disclosed herein, for example, from about 0° C. to about 400° C., or from about 25° C. to about 300° C.

Embodiment 24

The method defined in any of embodiments 20-22, wherein the halogen purge step is conducted for a time period in any range of halogen purge time periods disclosed herein, for example, from about 1 to about 48 hours.

Embodiment 25

The method defined in any of embodiments 20-24, wherein the halogen purge step is conducted for a time period sufficient to reduce the fluorine content of the outgoing halogen purge stream, after contacting the fluorinated spent catalyst, to less than any maximum fluorine content described herein, for example, less than about 100 ppmw of fluorine-containing compounds.

Embodiment 26

The method defined in any of embodiments 20-24, wherein the halogen purge step is conducted for a time period sufficient to reduce the chlorine content of the outgoing halogen purge stream, after contacting the chlorinated spent catalyst, to less than any maximum chlorine content described herein, for example, less than about 100 ppmw of chlorine-containing compounds.

Embodiment 27

A reforming method comprising:
(a) contacting a hydrocarbon feed with an aromatization catalyst comprising a transition metal and a catalyst support under reforming conditions in a reactor system to produce an aromatic product;
(b) performing step (a) for a time period sufficient to form a spent aromatization catalyst;
(c) contacting the spent aromatization catalyst with a halogen-containing stream comprising chlorine and fluorine to produce a halogenated spent catalyst; and
(d) contacting the halogenated spent catalyst with a decoking gas stream comprising oxygen.

Embodiment 28

The method defined in embodiment 27, wherein the reforming method is an in situ process, for example, steps (a)-(d) are performed in the same reactor system.

Embodiment 29

The method defined in embodiment 27, wherein steps (c)-(d) are performed externally to the reactor system of steps (a)-(b), for example, steps (c)-(d) are performed in a vessel that is not in the reforming reactor system.

Embodiment 30

The method defined in any of embodiments 27-29, further comprising a step of reactivating the catalyst after step (d).

Embodiment 31

A method of treating (or regenerating) a spent catalyst comprising a transition metal and a catalyst support, the method comprising:
(i) contacting the spent catalyst with a halogen-containing stream comprising chlorine and fluorine to produce a halogenated spent catalyst; and
(ii) contacting the halogenated spent catalyst with a decoking gas stream comprising oxygen.

Embodiment 32

The method defined in any of the preceding embodiments, wherein the catalyst support comprises a zeolite, an amorphous inorganic oxide, or any combination thereof.

Embodiment 33

The method defined in any of the preceding embodiments, wherein the catalyst support comprises an L-zeolite, a Y-zeolite, a mordenite, an omega zeolite, and/or a beta zeolite.

Embodiment 34

The method defined in any of the preceding embodiments, wherein the catalyst support comprises a potassium L-zeolite or a barium ion-exchanged L-zeolite.

Embodiment 35

The method defined in any of the preceding embodiments, wherein the spent catalyst comprises a support matrix comprising alumina, silica, a mixed oxide thereof, or a mixture thereof.

Embodiment 36

The method defined in any of the preceding embodiments, wherein the transition metal comprises a Group VIII transition metal.

Embodiment 37

The method defined in any of the preceding embodiments, wherein the transition metal comprises platinum.

Embodiment 38

The method defined in any of the preceding embodiments, wherein the spent catalyst comprises any weight percentage range of transition metal disclosed herein, for example, from about 0.1 wt. % to about 10 wt. %, or from about 0.3 wt. % to about 5 wt. %, transition metal, based on the weight of the spent catalyst excluding carbon.

Embodiment 39

The method defined in any of the preceding embodiments, wherein the spent catalyst comprises any weight percentage range of platinum disclosed herein, for example, from about 0.1 wt. % to about 10 wt. %, or from about 0.5 wt. % to about 2 wt. %, platinum, based on the weight of the spent catalyst excluding carbon.

Embodiment 40

The method defined in any of the preceding embodiments, wherein the spent catalyst comprises platinum on a KL-zeolite.

Embodiment 41

The method defined in any of the preceding embodiments, wherein the spent catalyst further comprises chlorine and fluorine.

Embodiment 42

The method defined in embodiment 41, wherein the spent catalyst comprises any weight percentage range of chlorine and/or weight percentage range of fluorine disclosed herein, for example, from about 0.025 wt. % to about 5 wt. % fluorine and/or from about 0.025 wt. % to about 5 wt. % chlorine, based on the weight of the spent catalyst excluding carbon.

Embodiment 43

The method defined in any of embodiments 1-26 or 41-42, wherein the spent catalyst comprises any molar ratio of chlorine:fluorine disclosed herein, for example, from about 0.5:1 to about 4:1.

Embodiment 44

The method defined in any of embodiments 27-43, wherein the molar ratio of Cl:F in the halogen-containing stream is in any range of molar ratios disclosed herein, for example, from about 0.2:1 to about 10:1.

Embodiment 45

The method defined in any of embodiments 27-44, wherein the halogen-containing stream comprises a chlorine-containing compound and a fluorine-containing compound.

Embodiment 46

The method defined in any of embodiments 1-26 or 45, wherein the chlorine-containing compound comprises hydrochloric acid, chlorine gas ($Cl_2$), carbon tetrachloride, tetrachloroethylene, chlorobenzene, methyl chloride, methylene chloride, chloroform, allyl chloride, trichloroethylene, a chloramine, a chlorine oxide, a chlorine acid, chlorine dioxide, dichlorine monoxide, dichlorine heptoxide, chloric acid, perchloric acid, ammonium chloride, tetramethylammonium chloride, tetraethylammonium chloride, tetrapropylammonium chloride, tetrabutylammonium chloride, methyltriethylammonium chloride, or any combination thereof.

Embodiment 47

The method defined in any of embodiments 1-26 or 45-46, wherein the chlorine-containing compound comprises chlorine gas ($Cl_2$).

Embodiment 48

The method defined in any of embodiments 1-26 or 45-47, wherein the fluorine-containing compound comprises hydrofluoric acid, fluorine gas, 2,2,2-trifluoroethanol, tetrafluoroethylene, carbon tetrafluoride, carbon trifluoride, fluoromethane, heptafluoropropane, decafluorobutane, hexafluoroisopropanol, tetrafluoropropanol, pentafluoropropanol, hexafluorophenylpropanol, perfluorobutyl alcohol, hexafluor-2-propanol, pentafluoro-1-propanol, tetrafluoro-1-propanol, 1,1,1,3,3,3-hexafluoro-2-propanol, 2,2,3,3,3-pentafluoro-1-propanol, ammonium fluoride, tetramethylammonium fluoride, tetraethylammonium fluoride, tetrapropylammonium fluoride, tetrabutylammonium fluoride, methyltriethylammonium fluoride or any combination thereof.

Embodiment 49

The method defined in any of embodiments 1-26 or 45-48, wherein the fluorine-containing compound comprises fluorine gas ($F_2$).

Embodiment 50

The method defined in any of embodiments 27-49, wherein the halogen-containing stream comprises a chlorine/fluorine-containing compound or chlorofluorocarbon.

Embodiment 51

The method defined in any of embodiments 27-50, wherein the halogen-containing stream comprises (or consists essentially of, or consists of) chlorine, fluorine, and any inert gas disclosed herein, for example, nitrogen.

Embodiment 52

The method defined in any of embodiments 27-51, wherein the halogen-containing stream comprises (or consists essentially of, or consists of) chlorine gas ($Cl_2$), fluorine gas ($F_2$), and nitrogen.

Embodiment 53

The method defined in any of embodiments 27-52, wherein the halogen-containing stream comprises a concentration of chlorine (Cl) and a concentration of fluorine (F) less than any maximum amount or in any range disclosed herein, for example, less than about 25,000 ppmv, in a range from about 50 to about 2,500 ppmv, or in a range from about 250 to about 2,000 ppmv.

Embodiment 54

The method defined in any of embodiments 27-53, wherein the halogen-containing stream is substantially free of oxygen-containing compounds, for example, less than 100 ppmw.

Embodiment 55

The method defined in any of embodiments 27-54, wherein the halogenation step is conducted at a halogenation temperature in any halogenation temperature range disclosed herein, for example, from about 0° C. to about 500° C., from about 25° C. to about 250° C., or from about 50° C. to about 280° C.

Embodiment 56

The method defined in any of embodiments 27-55, wherein the halogenation step is conducted for a time period in any range of halogenation time periods disclosed herein, for example, from about 1 to about 48 hours, from about 1 to about 12 hours, or from about 2 to about 8 hours.

Embodiment 57

The method defined in any of the preceding embodiments, wherein the decoking gas stream comprises (or consists essentially of, or consists of) any combination of an inert gas (one or more) and oxygen disclosed herein, for example, a mixture of nitrogen and oxygen, air, etc.

Embodiment 58

The method defined in any of the preceding embodiments, wherein the decoking gas stream comprises a mole % of oxygen less than any maximum amount or in any range disclosed herein, for example, less than about 5 mole %, or in a range from about 0.5 to about 3 mole %.

Embodiment 59

The method defined in any of the preceding embodiments, wherein the decoking gas stream is substantially free of halogen-containing compounds (substantially halogen-free), for example, less than 100 ppmw.

Embodiment 60

The method defined in any of the preceding embodiments, wherein the decoking gas stream is substantially free of water, for example, less than 100 ppmw.

Embodiment 61

The method defined in any of the preceding embodiments, wherein the carbon burn step is conducted at a peak decoking temperature in any peak decoking temperature range disclosed herein, for example, from about 300° C. to about 600° C., or from about 350° C. to about 450° C.

Embodiment 62

The method defined in any of the preceding embodiments, wherein the carbon burn step is started at an initial decoking temperature which is the same as any halogenation, fluorination, or chlorination temperature disclosed herein, for example, in a range from about 0° C. to about 500° C., from about 25° C. to about 250° C., or from about 50° C. to about 280° C.

Embodiment 63

The method defined in any of the preceding embodiments, wherein the carbon burn step is conducted for a time period in any range of de-coking time periods disclosed herein, for example, from about 1 to about 48 hours, or from about 1 to about 6 hours.

Embodiment 64

The method defined in any of the preceding embodiments, wherein the carbon burn step is conducted for a time period sufficient to reduce the wt. % of carbon on the halogenated spent catalyst (or fluorinated-chlorinated spent catalyst, or chlorinated-fluorinated spent catalyst) to less than any maximum weight percentage of carbon disclosed herein, for example, less than about 1 wt. %.

Embodiment 65

The method defined in any of the preceding embodiments, wherein the method further comprises a partial decoking step prior to the halogenation, fluorination, or chlorination step, the partial decoking step comprising contacting the spent catalyst with a partial decoking gas stream comprising oxygen.

Embodiment 66

The method defined in embodiment 65, wherein the partial decoking gas stream comprises (or consists essentially of, or consists of) any combination of an inert gas (one or more) and oxygen disclosed herein, for example, a mixture of nitrogen and oxygen, air, etc.

Embodiment 67

The method defined in any of embodiments 65-66, wherein the partial decoking gas stream comprises a mole % of oxygen less than any maximum amount or in any range disclosed herein, for example, less than about 5 mole %, or in a range from about 0.5 to about 3 mole %.

Embodiment 68

The method defined in any of embodiments 65-67, wherein the partial decoking gas stream is substantially free of halogen-containing compounds (substantially halogen-free), for example, less than 100 ppmw.

Embodiment 69

The method defined in any of embodiments 65-68, wherein the decoking gas stream is substantially free of water, for example, less than 100 ppmw.

Embodiment 70

The method defined in any of embodiments 65-69, wherein the partial decoking step is conducted at a partial decoking temperature in any partial decoking temperature range disclosed herein, for example, from about 150° C. to about 250° C.

Embodiment 71

The method defined in any of embodiments 65-70, wherein the partial decoking step is conducted for a time period in any range of partial de-coking time periods disclosed herein, for example, from about 2 to about 24 hours.

Embodiment 72

The method defined in any of embodiments 65-71, wherein the partial decoking step is conducted for a time period sufficient to reduce the wt. % of carbon on the spent catalyst to any range of weight percentage of carbon disclosed herein, for example, from about 1 to 10 wt. %, or from about 4 to about 5 wt. %.

Embodiment 73

The method defined in any of the preceding embodiments, wherein the method further comprises a pre-drying step prior to the halogenation, fluorination, or chlorination step, the pre-drying step comprising contacting the spent catalyst with a pre-drying gas stream comprising (or consisting essentially of, or consisting of) any inert gas disclosed herein, for example, nitrogen.

Embodiment 74

The method defined in embodiment 73, wherein the pre-drying gas stream is substantially free of oxygen-containing compounds, for example, less than 100 ppmw.

Embodiment 75

The method defined in any of embodiments 73-74, wherein the pre-drying step is conducted at a pre-drying temperature in any pre-drying temperature range disclosed herein, for example, from about 100° C. to about 500° C., from about 0° C. to about 400° C., or from about 180° C. to about 280° C.

Embodiment 76

The method defined in any of embodiments 73-75, wherein the pre-drying step is conducted for a time period in any range of pre-drying time periods disclosed herein, for example, from about 1 to about 48 hours.

Embodiment 77

The method defined in any of embodiments 73-76, wherein the pre-drying step is conducted for a time period sufficient to reduce the moisture content of the spent catalyst to less than any maximum moisture content of the spent catalyst disclosed herein, for example, less than about 4 wt. %, or less than about 1 wt. %.

Embodiment 78

The method defined in any of the preceding embodiments, wherein the method further comprises a re-coking pretreatment step prior to the halogenation, fluorination, or chlorination step, the re-coking pretreatment step comprising contacting the spent catalyst with a pretreatment stream comprising a hydrocarbon feed and molecular hydrogen.

Embodiment 79

The method defined in embodiment 78, wherein the hydrocarbon feed comprises $C_6$-$C_8$ alkanes and/or cycloalkanes.

Embodiment 80

The method defined in any of embodiments 78-79, wherein the pretreatment step is conducted at a pretreatment temperature in any pretreatment temperature range disclosed herein, for example, from about 100° C. to about 600° C.

Embodiment 81

The method defined in any of embodiments 78-80, wherein the pretreatment step is conducted for a time period in any range of pretreatment time periods disclosed herein, for example, from about 1 to about 48 hours.

Embodiment 82

The method defined in any of embodiments 78-81, wherein the pretreatment step is conducted for a time period sufficient to add any range of weight percentage of coke or carbon build-up to the spent catalyst disclosed herein, for example, from about 1 to about 2 wt. %.

Embodiment 83

The method defined in any of the preceding embodiments, wherein the method further comprises a purging step prior to the carbon burn step, the purging step comprising contacting the halogenated spent catalyst (or fluorinated-chlorinated spent catalyst, or chlorinated-fluorinated spent catalyst) with a purging stream comprising (or consisting essentially of, or consisting of) any inert gas disclosed herein, for example, nitrogen.

Embodiment 84

The method defined in embodiment 83, wherein the purging stream is substantially free of oxygen-containing compounds, for example, less than 100 ppmw.

Embodiment 85

The method defined in any of embodiments 83-84, wherein the purging stream is substantially free of halogen-containing compounds (substantially halogen-free), for example, less than 100 ppmw.

Embodiment 86

The method defined in any of embodiments 83-85, wherein the purging step is conducted at a purging temperature in any purging temperature range disclosed herein, for example, from about 0° C. to about 400° C., from about 25° C. to about 300° C., or from about 180° C. to about 280° C.

Embodiment 87

The method defined in any of embodiments 83-86, wherein the purging step is conducted for a time period in any range of purging time periods disclosed herein, for example, from about 1 to about 48 hours.

Embodiment 88

The method defined in any of embodiments 83-87, wherein the purging step is conducted for a time period sufficient to reduce the halogen content of the outgoing purging stream, after contacting the halogenated spent catalyst (or the fluorinated-chlorinated spent catalyst, or the chlorinated-fluorinated spent catalyst), to less than any maximum halogen content described herein, for example, less than about 100 ppmw of halogen-containing compounds.

Embodiment 89

The method defined in any of the preceding embodiments, wherein the method further comprises a hydrocarbon treatment step prior to the carbon burn step, the hydrocarbon treatment step comprising contacting the halogenated spent catalyst (or fluorinated-chlorinated spent catalyst, or chlorinated-fluorinated spent catalyst) with a hydrocarbon treatment stream comprising a hydrocarbon feed.

Embodiment 90

The method defined in embodiment 89, wherein the hydrocarbon feed comprises $C_6$-$C_8$ alkanes and/or cycloalkanes.

Embodiment 91

The method defined in any of embodiments 89-90, wherein the hydrocarbon treatment step is conducted at a hydrocarbon treatment temperature in any hydrocarbon treatment temperature range disclosed herein, for example, from about 400° C. to about 600° C.

Embodiment 92

The method defined in any of embodiments 89-91, wherein the hydrocarbon treatment step is conducted for a time period in any range of hydrocarbon treatment time periods disclosed herein, for example, from about 1 to about 48 hours.

Embodiment 93

The method defined in any of the preceding embodiments, wherein the method further comprises a reducing step after the carbon burn step, the reducing step comprising contacting the de-coked catalyst with a reducing gas stream comprising (or consisting essentially of, or consisting of) molecular hydrogen.

Embodiment 94

The method defined in embodiment 93, wherein the reducing gas stream comprises a mole % of molecular hydrogen greater than any minimum amount or in any range disclosed herein, for example, greater than about 25 mole %, or greater than about 75 mole %.

Embodiment 95

The method defined in any of embodiments 93-94, wherein the reducing step is conducted at a peak reducing temperature in any peak reducing temperature range disclosed herein, for example, from about 400° C. to about 600° C.

Embodiment 96

The method defined in any of embodiments 93-95, wherein the reducing step is started at an initial reducing temperature which is the same as any halogenation, fluorination, or chlorination temperature disclosed herein, for example, in a range from about 0° C. to about 500° C., from about 25° C. to about 250° C., or from about 50° C. to about 280° C.

Embodiment 97

The method defined in any of embodiments 93-96, wherein the reducing step is conducted for a time period in any range of reducing step time periods disclosed herein, for example, from about 10 to about 30 hours.

Embodiment 98

A reactivated or rejuvenated catalyst produced by the method defined in any of the preceding embodiments.

Embodiment 99

The catalyst defined in embodiment 98, wherein the reactivated or rejuvenated catalyst has an activity from about 50% to about 80% of the catalyst activity of fresh aromatization catalyst of the same production run of catalyst, when tested on the same equipment, and under the same method and test conditions.

Embodiment 100

The catalyst defined in any of embodiments 98-99, wherein the reactivated or rejuvenated catalyst has a fouling rate that is equal to or less than that of fresh aromatization catalyst from the same production run of catalyst.

Embodiment 101

The catalyst defined in any of embodiments 98-100, wherein the reactivated or rejuvenated catalyst has an EOR temperature that is within +/−8° C. of the EOR temperature of the fresh aromatization catalyst from the same production run of catalyst.

That which is claimed is:

1. A method of treating a spent catalyst comprising platinum and a catalyst support, the method comprising:
   (i) contacting the spent catalyst with a pre-drying gas stream consisting essentially of an inert gas;
   (ii) contacting the spent catalyst with a chlorine-containing stream comprising a chlorine-containing compound to produce a chlorinated spent catalyst;
   (iii) contacting the chlorinated spent catalyst with a fluorine-containing stream comprising a fluorine-containing compound to produce a chlorinated-fluorinated spent catalyst;
   (iv) contacting the chlorinated-fluorinated spent catalyst with a purging stream consisting essentially of an inert gas; and
   (v) contacting the chlorinated-fluorinated spent catalyst with a decoking gas stream comprising oxygen to produce a de-coked catalyst.

2. The method of claim 1, wherein the spent catalyst comprises from about 0.1 wt. % to about 10 wt. % platinum.

3. The method of claim 2, wherein the spent catalyst comprises:
   from about 0.5 to about 2 wt. % platinum;
   from about 0.025 wt. % to about 5 wt. % chlorine;
   from about 0.025 wt. % to about 5 wt. % fluorine; and
   a catalyst support comprising a bound medium and/or large pore zeolite and a support matrix.

4. The method of claim 2, wherein the pre-drying gas stream consists essentially of nitrogen.

5. The method of claim 2, wherein:
   step (ii) is conducted at a chlorination temperature in a range from about 25° C. to about 250° C.;
   a concentration of chlorine (Cl) in the chlorine-containing stream is in a range from about 50 to about 25,000 ppm by volume; and
   the chlorine-containing stream comprises $Cl_2$ and nitrogen, and is substantially free of oxygen-containing compounds.

6. The method of claim 2, wherein:
   step (iii) is conducted at a fluorination temperature in a range from about 10° C. to about 100° C.;
   a concentration of fluorine (F) in the fluorine-containing stream is in a range from about 50 to about 25,000 ppm by volume; and
   the fluorine-containing stream comprises $F_2$ and nitrogen, and is substantially free of oxygen-containing compounds.

7. The method of claim 2, wherein the purging stream consists essentially of nitrogen.

8. The method of claim 2, wherein:
   step (v) is conducted at a peak decoking temperature in a range from about 300° C. to about 500° C.;
   the decoking gas stream comprises air or a mixture of nitrogen and oxygen; and
   the decoking gas stream is substantially free of halogen-containing compounds.

9. A rejuvenated catalyst produced by the method of claim 2.

10. The method of claim 2, further comprising a halogen purge step prior to step (iii), the halogen purge step comprising contacting the chlorinated spent catalyst with a halogen purge stream consisting essentially of an inert gas.

11. The method of claim 2, further comprising:
a partial decoking step prior to step (ii), the partial decoking step comprising contacting the spent catalyst with a partial decoking gas stream comprising oxygen at a partial decoking temperature in a range from about 150° C. to about 250° C.; and
a reducing step after step (v), the reducing step comprising contacting the de-coked catalyst with a reducing gas stream comprising molecular hydrogen.

12. A rejuvenated catalyst produced by the method of claim 11.

13. The method of claim 1, wherein the spent catalyst comprises platinum and one or more transition metals selected from iron, cobalt, nickel, ruthenium, rhodium, palladium, osmium, iridium, gold, silver, copper, or mixtures thereof.

14. A reforming process comprising:
(a) contacting a hydrocarbon feed with an aromatization catalyst comprising platinum and a catalyst support under reforming conditions in a reactor system to produce an aromatic product;
(b) performing step (a) for a time period sufficient to form a spent aromatization catalyst;
(c) contacting the spent aromatization catalyst with a pre-drying gas stream consisting essentially of an inert gas;
(d) contacting the spent aromatization catalyst with a chlorine-containing stream comprising a chlorine-containing compound to produce a chlorinated spent catalyst;
(e) contacting the chlorinated spent catalyst with a fluorine-containing stream comprising a fluorine-containing compound to produce a chlorinated-fluorinated spent catalyst;
(f) contacting the chlorinated-fluorinated spent catalyst with a purging stream consisting essentially of an inert gas; and
(g) contacting the chlorinated-fluorinated spent catalyst with a decoking gas stream comprising oxygen to produce a de-coked catalyst.

15. The process of claim 14, wherein the aromatization catalyst comprises from about 0.1 wt. % to about 10 wt. % platinum.

16. The process of claim 15, wherein the aromatization catalyst comprises:
from about 0.5 to about 2 wt. % platinum;
from about 0.025 wt. % to about 5 wt. % chlorine;
from about 0.025 wt. % to about 5 wt. % fluorine; and
a catalyst support comprising a bound medium and/or large pore zeolite and a support matrix.

17. The process of claim 15, wherein:
step (d) is conducted at a chlorination temperature in a range from about 25° C. to about 250° C.;
a concentration of chlorine (Cl) in the chlorine-containing stream is less than about 2,500 ppm by volume;
the chlorine-containing stream comprises $Cl_2$ and nitrogen, and is substantially free of oxygen-containing compounds;
step (e) is conducted at a fluorination temperature in a range from about 10° C. to about 100° C.;
a concentration of fluorine (F) in the fluorine-containing stream is less than about 2,500 ppm by volume; and
the fluorine-containing stream comprises $F_2$ and nitrogen, and is substantially free of oxygen-containing compounds.

18. The process of claim 15, wherein the reforming process is an in situ process.

19. The process of claim 15, wherein steps (d)-(g) are performed in a vessel external to the reactor system.

20. The process of claim 14, wherein the aromatization catalyst comprises platinum and one or more transition metals selected from iron, cobalt, nickel, ruthenium, rhodium, palladium, osmium, iridium, gold, silver, copper, or mixtures thereof.

* * * * *